US011806230B2

(12) United States Patent
Kintzing et al.

(10) Patent No.: US 11,806,230 B2
(45) Date of Patent: Nov. 7, 2023

(54) SYSTEMS AND METHODS FOR ALTERING THE SHAPE OF NASAL TISSUES

(71) Applicants: THE BOARD OF TRUSTEES OF THE LELAND STANFORD JUNIOR UNIVERSITY, Stanford, CA (US); The U.S. Government, The Department of Veterans Affairs, Washington, DC (US); The Mayo Foundation for Medical Education and Research, Rochester, MN (US)

(72) Inventors: James Kintzing, San Jose, CA (US); McCutcheon Brandon, Rochester, MN (US); Nayak Jayakar, Stanford, CA (US)

(73) Assignee: The Board of Trustees of the Leland Stanford Jr. University, Stanford, CA (US)

( * ) Notice: Subject to any disclaimer, the term of this patent is extended or adjusted under 35 U.S.C. 154(b) by 240 days.

(21) Appl. No.: 17/344,848

(22) Filed: Jun. 10, 2021

(65) Prior Publication Data
US 2022/0000609 A1 Jan. 6, 2022

Related U.S. Application Data

(60) Provisional application No. 63/110,898, filed on Nov. 6, 2020, provisional application No. 63/068,308, filed (Continued)

(51) Int. Cl.
*A61F 2/18* (2006.01)
*A61F 2/28* (2006.01)

(52) U.S. Cl.
CPC ............ *A61F 2/186* (2013.01); *A61F 2/2875* (2013.01); *A61F 2002/2885* (2013.01); *A61F 2210/0014* (2013.01); *A61F 2220/0016* (2013.01)

(58) Field of Classification Search
CPC .................... A61F 2/186; A61F 2/2875; A61F 2002/2885; A61F 2220/0016
See application file for complete search history.

(56) References Cited

U.S. PATENT DOCUMENTS 6,626,172 B1 9/2003 Karow et al.
7,438,208 B2 10/2008 Larson
(Continued)

FOREIGN PATENT DOCUMENTS

| CA | 2811967 | 4/2012 |
| WO | 2006112678 A1 | 10/2006 |
| WO | 2014134185 A1 | 9/2014 |

OTHER PUBLICATIONS

Jung, Da Won, Authorized officer from Korean Intellectual Property Office, International Search Report and Written Opinion from corresponding International application No. PCT/US2021/036881, dated Oct. 1, 2021, 14 pages.

*Primary Examiner* — Suba Ganesan
(74) *Attorney, Agent, or Firm* — William A. English; Vista IP Law Group LLP

(57) ABSTRACT

Systems and methods are provided for altering the shape of a target tissue structure of a subject, e.g., a nasal septum or other nasal tissue that include securing a first end of a shaping element to tissue adjacent the structure; manipulating the tissue to alter a shape of the structure; and applying a force to the shaping element to maintain the altered shape of the structure.

19 Claims, 36 Drawing Sheets

Related U.S. Application Data on Aug. 20, 2020, provisional application No. 63/037,532, filed on Jun. 10, 2020.

(56) References Cited

U.S. PATENT DOCUMENTS

| | | | |
|---|---|---|---|
| 7,641,688 B2 | 1/2010 | Lesh | |
| 7,934,506 B2 | 5/2011 | Woodson et al. | |
| 7,972,379 B2 | 7/2011 | Jung et al. | |
| 8,216,311 B2 | 7/2012 | Kang et al. | |
| 8,267,962 B2 | 9/2012 | Stupak | |
| 8,413,662 B2 | 4/2013 | Metzger et al. | |
| 8,715,347 B2 | 5/2014 | Servell et al. | |
| 8,784,488 B2 | 7/2014 | Saidi | |
| 8,821,575 B2 | 9/2014 | Van Der Burg et al. | |
| 9,877,862 B2 | 1/2018 | Weadock et al. | |
| 9,895,252 B2 | 2/2018 | Awengen et al. | |
| 9,949,823 B2 | 4/2018 | Hristov et al. | |
| 10,835,412 B2 | 11/2020 | Krespi et al. | |
| 10,980,631 B2 | 4/2021 | Rosenthal et al. | |
| 11,135,083 B2 | 10/2021 | Dillard | |
| 2002/0173848 A1 | 11/2002 | Sachs | |
| 2004/0088003 A1 | 5/2004 | Leung et al. | |
| 2006/0276817 A1 | 12/2006 | Vassallo et al. | |
| 2007/0219575 A1 | 9/2007 | Mejia | |
| 2008/0027480 A1* | 1/2008 | van der Burg | A61B 17/0401 606/199 |
| 2008/0077240 A1* | 3/2008 | Saidi | A61F 5/08 623/10 |
| 2011/0251634 A1* | 10/2011 | Gonzales | A61B 17/064 606/199 |
| 2012/0310280 A1 | 12/2012 | Harrington | |
| 2013/0006293 A1* | 1/2013 | Smith | A61F 2/82 606/199 |
| 2014/0228971 A1 | 8/2014 | Kim | |
| 2018/0116648 A1 | 5/2018 | Kim | |
| 2020/0197171 A1 | 6/2020 | Saidi et al. | |
| 2020/0253726 A1 | 8/2020 | Saidi | |
| 2020/0315839 A1 | 10/2020 | Sanders | |
| 2021/0212813 A1 | 7/2021 | Baron et al. | |
| 2021/0315689 A1 | 10/2021 | Rosenthal et al. | |

* cited by examiner

SYSTEMS AND METHODS FOR ALTERING THE SHAPE OF NASAL TISSUES

CROSS-REFERENCE TO RELATED APPLICATIONS

This application claims priority to U.S. Provisional Application Ser. No. 63/037,532, filed Jun. 10, 2020, U.S. Provisional Application No. 63/068,308, filed Aug. 20, 2020, and U.S. 63/110,898, filed Nov. 6, 2020, the disclosures of which are herein incorporated by reference in their entirety.

FIELD

Described herein are systems and methods generally related to the field of Ear, Nose, and Throat (ENT) surgery, and more specifically to new and useful systems and methods for altering the shape of nasal tissues.

BACKGROUND

Nasal septal deviations occur in up to 75% of patients, with far fewer being symptomatic. When symptomatic, a deviated septum may cause nasal airway obstruction which impairs the patient's ability to breath. When symptoms are sufficiently severe the patient may require a septoplasty or septorhinoplasty surgery. Approximately 300,000-600,000 patients require this surgery in the United States every year. While many ENT surgeries have been transitioned to an office-based setting with minimally invasive approaches, septal surgery has fundamentally lagged behind; leaving patients and physicians looking for minimally invasive approaches.

Septal surgery is non-trivial. For the patient, it requires a trip to the operating room and general anesthesia. The recovery can also be significant, especially in the case of septorhinoplasty. For the surgeon, operating room (OR) based surgeries can present increased risks and costs while also introducing inefficiencies in the delivery of care. Therefore, both surgeons and patients may be interested in less invasive procedures that can be performed in a lower resource setting.

There are currently no minimally-invasive septal correction systems in clinical practice today. Thus, there is a need for new and useful systems and methods for reshaping the nasal septal cartilage. The systems and methods described herein provide for such an approach.

SUMMARY

Described herein are systems and methods in the field of ear, nose, and throat (ENT) surgery, and, more particularly to systems and methods for altering the shape of various tissue structures. For example, the systems and methods may be used to reshape nasal tissues. A device including a tensioning element (shaping element) may be employed to apply tension to a tissue or maintain force on an engaged tissue to thereby alter tissue shape.

The systems for shaping a tissue structure of a subject may include an elongate member comprising a proximal end, a distal end sized for introduction into the subject's body, and a lumen extending between the proximal end and a port in the distal end, and a shaping element. The shaping element may include a first end sized for introduction through the lumen to deploy the first end out the port to engage tissue adjacent the tissue structure, a second end opposite the first end, and one or more elements to maintain a force on the engaged tissue to alter the shape of the tissue structure.

In some instances, the systems for shaping a tissue structure of a subject may include an elongate member comprising a proximal end, a distal end sized for introduction into the subject's body, and a lumen extending between the proximal end and a port at the distal end, and a needle removably coupled to the elongate member. A shaping element may further be included that comprises a first end deployable from the port to engage tissue at a first location adjacent the tissue structure, and a second end carried by the needle for securing the second end to tissue at a second location adjacent the tissue structure, and one or more elements to maintain tension on the engaged tissue to alter the shape of the tissue structure.

Other embodiments of the systems for shaping a tissue structure of a subject may include an elongate member comprising a proximal end, a distal end sized for introduction into the subject's body, and a lumen extending between the proximal end and a port at the distal end, a needle removably coupled to the elongate member, and a shaping element. The shaping element may include a first end deployable from the port to engage tissue at a first location adjacent the tissue structure, and a second end carried by the needle for securing the second end to tissue at a second location adjacent the tissue structure, and one or more elements to maintain tension on the engaged tissue to alter the shape of the tissue structure.

In some embodiments, the systems for shaping a tissue structure of a subject may include an elongate member comprising a proximal end, a distal end sized for introduction into the subject's body, a lumen extending between the proximal end and the distal end, a first port at the distal end, and a second port located proximal to the first port, and a shaping element. The shaping element may comprise a first end deployable from the first port to engage tissue at a first location adjacent the tissue structure, and a second end deployable from the second port to engage tissue at a second location adjacent the tissue structure, and one or more elements to maintain tension on the engaged tissue to alter the shape of the tissue structure.

Methods for altering the shape of tissue structures of a subject are also described herein. In accordance with an exemplary embodiment, the method may employ a device that includes an elongate member comprising a proximal end, a distal end sized for introduction into the subject's body, and a lumen extending between the proximal end and a port in the distal end, and a shaping element. The shaping element may include a first end sized for introduction through the lumen to deploy the first end out the port to engage tissue adjacent the tissue structure, a second end opposite the first end, and one or more elements to maintain a force on the engaged tissue to alter the shape of the tissue structure.

Methods are also provided for altering the shape of nasal tissue of a subject that include inserting a distal end of a delivery device into a nasal airway of the subject, deploying a first end of a shaping element from the distal end into the nasal airway; securing the first end of the shaping element to tissue adjacent the nasal airway, manipulating the shaping element to alter a shape of the tissue, and removing the delivery device such that the shaping element at least temporarily maintains the altered shape of the tissue.

Additionally, methods are provided for altering the shape of nasal tissue of a subject that include deploying a first end of a shaping element into a nasal airway of the subject, securing the first end of the shaping element to tissue at a first location adjacent the nasal airway, manipulating the shaping element to alter a shape of the tissue, and securing the shaping element relative to tissue at a second location to maintain the altered shape of the tissue.

Further described herein are methods for altering the shape of a target tissue structure of a subject that include securing a first end of a shaping element to tissue adjacent the structure; manipulating the tissue to alter a shape of the structure, and applying a force to the shaping element to maintain the altered shape of the structure.

In accordance with other embodiments, methods are described that provide for altering the shape of nasal tissue of a subject including the steps of introducing an anchor into a nasal airway of the subject, securing the anchor at a first location to a nasal septum of the subject, introducing a first end of a shaping element into a nasal airway of the subject, securing the first end of the shaping element to the anchor, manipulating the shaping element to alter a shape of the tissue, and securing the shaping element relative to tissue at a second location to maintain the altered shape of the tissue.

The methods for altering the shape of nasal tissue of a subject described herein may also include inserting a distal end of a delivery device into a nasal airway of the subject, deploying a first end of a shaping element from the distal end into the nasal airway, securing the first end of the shaping element to tissue at a first location adjacent the nasal airway, removing the delivery device such that the shaping element extends from nasal airway, inserting a needle coupled to a second end of the shaping element into the nasal airway, manipulating the shaping element to alter a shape of the tissue, and securing the second end at a second location adjacent the nasal airway to at least temporarily maintain the altered shape of the tissue.

BRIEF DESCRIPTION OF THE DRAWINGS

Illustrative aspects of the present disclosure are described in detail below with reference to the following drawings. It will be appreciated that the exemplary devices shown in the drawings are not necessarily drawn to scale, with emphasis instead being placed on illustrating the various features of the illustrated embodiments.

In FIG. 12, the delivery device includes a tip for housing a tensioning element. The delivery device shown in FIG. 13 includes a pistol grip.

In FIG. 27, the tensioning element includes an enlarged distal end that interfaces with a securing element; and in FIG. 28, the securing element includes a tissue interaction feature designed to catch on tissue.

DETAILED DESCRIPTION

Figure 1:
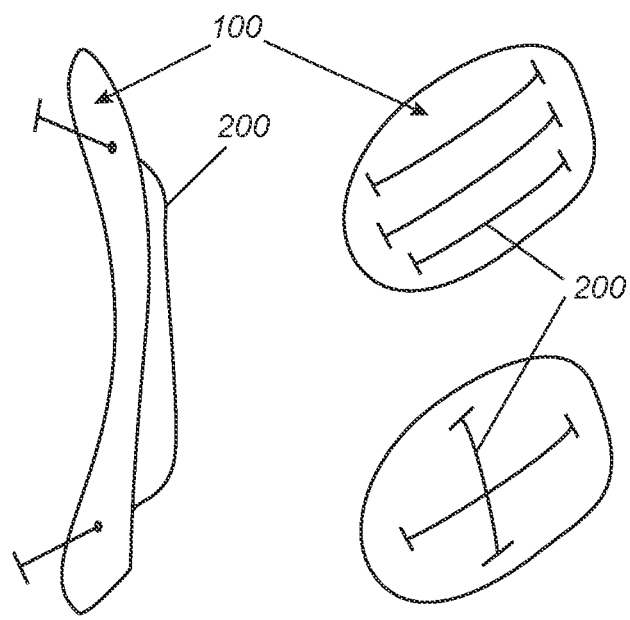
FIG. 1 depicts an exemplary tensioning element for use in altering the shape of a nasal tissue.

Disclosed herein are systems and methods for altering the shape of various body tissues. For example, the systems and methods may be used to reshape nasal tissues such as nasal septal cartilage, lateral nasal cartilage, a major or minor alar cartilage, alar fibrofatty tissue, a nasal bone, and a nasal turbinate. The systems generally include a device comprising a tensioning element (shaping element) configured to apply tension to a tissue or maintain force on an engaged tissue to thereby alter tissue shape. In addition, the systems may include accessory devices that aid in cutting or grinding tissue to shape the tissue, or accessory devices that help displace or move tissue into a position for securement by a tensioning element. Devices for delivering one or more tensioning elements are also described herein.

Systems

The systems generally include one or more tensioning elements or shaping elements configured to apply and maintain a force against tissue to alter the shape of the tissue. The force may be a tension force. The tensioning element may include an elongate body having a proximal end, a distal end, a relaxed state, and a tensioned state. At the distal end, a securing element may be coupled to, or disposed on, the tensioning element to fix or anchor the tensioning element to a tissue. One or more migration prevention elements may be provided on the proximal end of the tensioning element to hold the tensioning element in its tensioned state after deployment. A needle may also be provided on the proximal end to direct or facilitate placement of the tensioning element through tissue.

In some embodiments, the systems for shaping a tissue structure of a subject may include an elongate member (e.g., an elongate member of a delivery device) comprising a proximal end, a distal end sized for introduction into the subject's body, and a lumen extending between the proximal end and a port in the distal end, and a shaping element. The shaping element may include a first end sized for introduction through the lumen to deploy the first end out the port to engage tissue adjacent the tissue structure, a second end opposite the first end, and one or more elements to maintain a force on the engaged tissue to alter the shape of the tissue structure.

The tensioning member may be made from various materials. Exemplary materials include without limitation, LPLA (Poly(L-lactide)), DLPLA (Poly(DL-lactide)), LDLPLA (Poly(DL-lactide-co-L-lactide)), LPLA-HA (Poly(L-lactide) with hydroxylapatite), PGA (Poly(glycolide)), PGA-TMC (Poly(glycolide-co-trimethylene carbonate) or polyglyconate), PDO (Poly(dioxanone)), LPLG (Poly(L-lactide-co-glycolide)), DLPLG (Poly(DL-lactide-co-glycolide), a copolymer of any of these or other suitable polymers, or any other suitable material. In one embodiment, the tensioning member is made from PDO (Poly (dioxanone)).

The length of the tensioning member may range from about 3.0 cm to about 30 cm, including all values and sub-ranges therein. For example, the length of the tensioning member may be about 3.0 cm, about 4.0 cm, about 5.0 cm, about 6.0 cm, about 8.0 cm, about 9.0 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, about 23 cm, about 24 cm, or about 25 cm. In one embodiment, the length of the tensioning member is about 15 cm.

The shaping element may include a securing element that anchors or fixes the shaping element to a tissue, for example, a nasal tissue. The securing element may be configured such that a first end of the shaping element may be directed through the tissue but prevented from passing back through the nasal tissue. In some embodiments, the securing element comprises one or more of a T-fastener, an X-shaped fastener, an expandable anchor, a button, a shape-retaining structure, a barb, and a plurality of barbs. In one embodiment, the securing element includes a plurality of barbs. In other embodiments, the securing element may be adjustable or slidable along the shaping element relative to the first end. In some instances, the shaping element may include a plurality of protrusions spaced from one another adjacent the first end. A securing element coupled to the shaping element may be configured to releasably engage the protrusions to adjust the position of the securing element relative to the first end.

One or more migration prevention elements may be provided between the first (distal) and second (proximal) ends of the shaping element to hold the shaping element in its tensioned state after deployment. In one embodiment, a plurality of migration prevention elements may be disposed closer to the second (proximal end) than to the first (distal) end. The one or more migration prevention elements may comprise a plurality of ratchet elements on a region of the shaping element spaced from the first end. A plurality of barbs may also be used as migration prevention elements. In some embodiments, the migration prevention elements may be a plurality of hooks, arrows, spherical-shaped elements, or other shaped elements disposed along the shaping element. Alternatively, the one or more migration prevention elements may be configured to allow the shaping element to be directed through tissue in a first direction but prevent passage in a second direction back through the tissue.

The systems may further include a force distribution region on the shaping element spaced from first end to provide atraumatic contact of the shaping element with tissue. In some embodiments, the force distribution region may have a width and/or surface area greater than the shaping element adjacent the force distribution region. The width of the force distribution region may range from about 0.25 mm to about 2.5 mm, including all values and sub-ranges therein. For example, the force distribution region width may be about 0.25 mm, about 0.50 mm, about 0.75 mm, about 1.0 mm, about 1.25 mm, about 1.5 mm, about 1.75 mm, about 2.0 mm, about 2.25 mm, or about 2.50 mm. In some embodiments, the force distribution region width may range from about 0.50 mm to about 1.0 mm. Delivery of the shaping elements to a target region of a tissue may be accomplished using suture techniques or via an elongate member, for example, an elongate member of a delivery device. The elongate member may have any length suitable to access the target tissue region and place the shaping element therein. In some embodiments, the length of the elongate member may range from about 3.0 cm to about 10 cm, including all values and sub-ranges therein. For example, the length of the elongate member may be about 3.0 cm, about 3.5 cm, about 4.0 cm, about 4.5 cm, about 5.0 cm, about 5.5 cm, about 6.0 cm, about 6.5 cm, about 7.0 cm, about 7.5 cm, about 8.0 cm, about 8.5 cm, about 9.0 cm, about 9.5 cm, or about 10 cm.

The elongate member may include one or more ports for deployment of the shaping element from the lumen of the elongate member. In one embodiment, the elongate member includes a single port. In another embodiment, the elongate member includes two ports. The one or more ports may be located on a sidewall of the distal end, and may be any suitable size and shape. For example, the ports may be circular, ovular, triangular, rectangular, square, slit-like, etc. In one embodiment, the system further includes a guide element sized for introduction into the lumen. The guide element may be movable relative to the elongate member for directing a tip of the guide element out the side port into tissue. The guide element may also include a guide interface, where the first end of the shaping element engages with the guide interface such that the first end is deployable from the tip. In some embodiments, the guide element comprises a needle terminating in a sharpened distal tip configured to penetrate through tissue. In other embodiments, the guide element may include a hollow needle with a lumen. The length of the guide element may range from about 3.0 cm to about 10 cm, including all values and sub-ranges therein. For example, the length of the elongate member may be about 3.0 cm, about 3.5 cm, about 4.0 cm, about 4.5 cm, about 5.0 cm, about 5.5 cm, about 6.0 cm, about 6.5 cm, about 7.0 cm, about 7.5 cm, about 8.0 cm, about 8.5 cm, about 9.0 cm, about 9.5 cm, or about 10 cm. In some embodiments, the length of the guide element ranges from about 9.0 cm to about 11 cm, including all values and sub-ranges therein.

The elongate member may further include an actuator on the proximal end of the elongate member for selectively directing the guide element from a proximal position, where the tip of the guide element is within the distal end of the elongate member, and a distal position, wherein the tip of the guide element extends out a side port. In one embodiment, the tip of the guide element may be biased to a curved shape to direct the tip laterally relative to the distal end of the elongate member. In another embodiment, the elongate member includes an imaging or visualization element on its distal end. Exemplary imaging and visualization elements include without limitation, a fiberoptic visualization system, CCD, CMOS or other camera. In a further embodiment, a handle may be provided at the proximal end of the elongate member, and include one or more actuators for deploying the shaping element.

In another embodiment, the system for shaping a tissue structure of a subject may include an elongate member comprising a proximal end, a distal end sized for introduction into the subject's body, and a lumen extending between the proximal end and a port at the distal end, and a needle removably coupled to the elongate member. A shaping element may further be included that comprises a first end deployable from the port to engage tissue at a first location adjacent the tissue structure, and a second end carried by the needle for securing the second end to tissue at a second location adjacent the tissue structure, and one or more elements to maintain tension on the engaged tissue to alter the shape of the tissue structure.

Other embodiments of the systems for shaping a tissue structure of a subject may include an elongate member comprising a proximal end, a distal end sized for introduction into the subject's body, and a lumen extending between the proximal end and a port at the distal end, a needle removably coupled to the elongate member, and a shaping element. The shaping element may include a first end deployable from the port to engage tissue at a first location adjacent the tissue structure, and a second end carried by the needle for securing the second end to tissue at a second location adjacent the tissue structure, and one or more elements to maintain tension on the engaged tissue to alter the shape of the tissue structure.

In yet a further embodiment, the system is for shaping a tissue structure of a subject may include an elongate member comprising a proximal end, a distal end sized for introduction into the subject's body, a lumen extending between the proximal end and the distal end, a first port at the distal end, and a second port located proximal to the first port, and a shaping element. The shaping element may comprise a first end deployable from the first port to engage tissue at a first location adjacent the tissue structure, and a second end deployable from the second port to engage tissue at a second location adjacent the tissue structure, and one or more elements to maintain tension on the engaged tissue to alter the shape of the tissue structure.

The shaping of nasal tissue may further be aided by the delivery of one or more fluids to the nasal tissue. In these embodiments, the tensioning element may be configured with a fluid delivery mechanism such as a conduit, channel, or other mechanism for suitable delivery of fluid to nasal tissue. This fluid delivery mechanism may allow for the passage of fluid to achieve a therapeutic or physiologic effect. The fluid may be water, phosphate buffered saline (PBS), balanced salt solution (BSS), 0.9% normal saline, lactated ringers solution, a local anesthetic such as lidocaine or procaine, or D5W (5% dextrose in water). The fluid delivery mechanism may also be used to deliver a cold gas or liquid for the purposes of cryotherapy. For example, the cold gas or liquid may include compressed air, $CO_2$, $N_2$, $N_2O$, chilled saline, a fluorinated hydrocarbon, or liquid chlorodifluoromethane.

Exemplary Systems

Described below are systems including a tensioning element for altering the shape of a nasal tissue. The tensioning element (200) functions to secure the nasal tissue in an altered state by applying a force, pressure, or tension to the nasal tissue. In some embodiments, the tensioning element may have variable physical properties, e.g., having a flexible or rigid shape, being formed from inelastic or elastic materials, and/or including multiple segments of differing rigidity and/or other mechanical properties. In embodiments where some or all of the tensioning element is rigid, the tensioning element may optionally be configured such that the shape is set and maintained just before or after fixation within the nasal tissue. In some embodiments, the shape may be modifiable as desired by the patient or as needed to obtain the required alteration in tissue shape. In some embodiments, the tensioning element may be configured with some or all portions of the tensioning element having shape memory or a tendency to return towards a preset shape when deflected. In some embodiments, the majority or entirety of the tensioning element is flexible and may exert tension on the nasal tissue when the tensioning element is secured in place. In some embodiments, the tensioning element may be applied directly on the tissue to be altered. In some embodiments, the tensioning element may be applied to tissue adjacent, deep, superficial, or bilateral to the nasal tissue to be altered. The tensioning element may be of any suitable size, shape, length, or width.

In some embodiments, the tensioning element is configured to be reversible or removable. In such embodiments, the tensioning element can be configured to have at least some portion accessible above the nasal mucosa. The accessible portion can specifically comprise the securing portion at the distal end of the tensioning element, configured to reside above the mucosa on the concave surface of the deviation, contralateral to the body of the tensioning element. Alternatively, the tensioning element can be configured to include another or additional accessible portion or portions. The accessible portion can specifically be configured to be removed or retrieved, such as by scissors or scalpel inserted into the nostril, such that the remainder of the tensioning element can be pulled out of the nasal tissue without the securing portion. Alternatively, the accessible portion can be configured to be removed by another suitable method of retrieval. In such reversible or removable embodiments, the tensioning element can be easily retrieved and removed from the nasal tissue to allow the procedure to be easily reversible.

In some embodiments, the tensioning element is used to correct a nasal septal deviation. In this case, the tensioning element may preferentially be delivered beneath the nasal septal mucosa on the convex curvature of a deviation, but may also be configured to be placed above the nasal septal mucosa. When delivered beneath the nasal septal mucosa, a delivery device may be used to anchor a securing element, such as a T-fastener located on the distal end of tensioning element relative to the nasal septal cartilage. The delivery device may accomplish this using a penetrating feature or other mechanism, e.g., formed from Nitinol, spring steel, and the like, designed to deploy the securing element. The securing element, when placed, may reside above or below the contralateral nasal septal mucosa. For example, the securing element may be placed at the distal most aspect of the deviation. The proximal end of the tensioning element may have a penetrating feature that allows the tensioning element to be passed across the nasal septum to the contralateral nasal airway. Alternatively, the proximal end of the tensioning element may be passed across the nasal septum by way of a penetrating feature on the delivery device. Between the distal securing element and the proximal end of the tensioning element there may be one or more securing elements such as barbs that are designed to prevent backwards migration of the tensioning element. The one or more proximal securing elements may be designed to allow the tensioning element to gradually correct a nasal septal deviation. For example, barbs along the length of the tensioning element could be gradually pulled through the nasal septal cartilage until the desired correction is achieved.

In some embodiments, the system used for correction of a nasal septal deviation with a tensioning element may be designed to maintain the structural integrity of the nasal septal cartilage without significantly weakening it.

Figure 6:
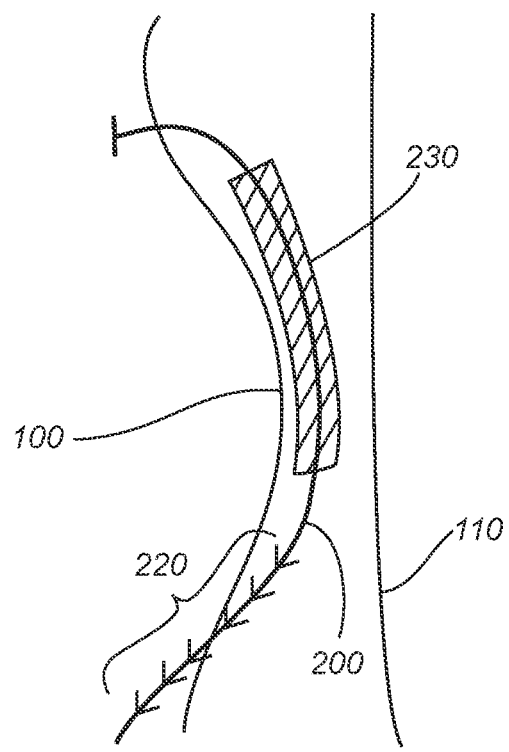
FIG. 6 depicts another exemplary tensioning element including a plurality of migration prevention elements and a force distributing region.

As shown in FIG. 6, in some embodiments, the tensioning element may contain one or more securing portions (210) at one or both ends. Optionally, the tensioning element may additionally or alternatively have one or more migration prevention elements (220) or one or more force distributing regions (230). Each of the migration prevention elements may take on the shape of a barb, ratchet, protrusion, or any other suitable configuration to prevent migration of the tensioning element, e.g., allowing the elements to be introduced through tissue in a first direction while preventing the elements from being pulled back through the tissue. The securing portion or portions (210) primarily functions to resist migration of the tensioning element through the nasal tissue and may be configured similar to a T-fastener, X-shaped fastener, expandable anchor, button, shape-retaining structure, barb, a plurality of barbs, or any other suitable structure for resisting movement. In some embodiments, the securing portion may be tension or position adjustable. In some embodiments, the tensioning element may be configured without the securing portions. The securing portion may be made of the same material or materials as the adjacent portion of the tensioning element or may be constructed from a different material or materials. The optional migration prevention element (220) may be configured as one or more barbs and may be arranged in a parallel or spiral pattern or in any arrangement suitable for securing the tensioning element. In some embodiments, such barbs may have fixed or variable sizes and may be composed of fixed or variable material or materials.

In some embodiments, the tensioning element may include barbs at one end; in other embodiments, the tensioning element may include barbs along multiple regions; in other embodiments, all or none of the tensioning element may include barbs. The force distributing region (230) primarily functions to increase surface area and distribute pressure across nasal tissues. The force distributing region may be fixed or variable length and may have a fixed or variable position on the tensioning element. For example, in some embodiments, the force distributing region may be fixed in position relative to the tensioning element or may slide on, off, along, or around the tensioning element. The force distributing region may be composed of the same material or materials as the adjacent portions of the tensioning element or may be composed of a different material or materials. In some embodiments, the tensioning element contains one force distributing region. In other embodiments, the tensioning element contains no force distributing regions or multiple force distributing regions. In some embodiments the tensioning element may have a needle at none, one, or a plurality of ends of the tensioning element. In some embodiments the needle or needles may be flat or curved. The needle or needles may be made of any suitable material to allow for the tensioning element to be passed through tissue.

In some embodiments, the tensioning element may be solid. In some embodiments, the tensioning agent may be porous or non-porous. In some embodiments, the tensioning element may be configured to promote tissue regrowth or prevent blood clot formation. The tensioning element may optionally be designed to be coated with, bonded to, impregnated with, or otherwise release a functional agent suitable for altering a physiological property. The functional agent may be configured as a therapeutic agent such as an antibiotic agent, anti-inflammatory agent, growth promoting agent, hemostatic agent, clot prevention agent, analgesic, or any suitable drug, molecule, or compound to achieve a therapeutic effect.

The tensioning element may be secured partially or entirely beneath a nasal mucosa (110) or maybe exposed within the nasal airway. In some embodiments, the tensioning element may be manufactured from a single material or may be a composite material composed of multiple materials. In some embodiments, the tensioning element may have a monofilament or suture-like structure. In other embodiments, the tensioning element may have a rod-like structure, a braided structure, a woven-structure, flat structure, or any other structure suitable for providing the desired mechanical properties. In some embodiments, all or a component of the tensioning element may be degradable, absorbable, resorbable, biodegradable, or bioabsorbable. Such embodiments may include components comprising LPLA (Poly(L-lactide)), DLPLA (Poly(DL-lactide)), LDLPLA (Poly(DL-lactide-co-L-lactide)), LPLA-HA (Poly(L-lactide) with hydroxylapatite), PGA (Poly(glycolide)), PGA-TMC (Poly (glycolide-co-trimethylene carbonate) or polyglyconate), PDO (Poly(dioxanone)), LPLG (Poly(L-lactide-co-glycolide)), DLPLG (Poly(DL-lactide-co-glycolide), a copolymer of any of these or other suitable polymers, or any other suitable material. In some embodiments, the tensioning element may be non-biodegradable or non-bioabsorbable or removable at a later point in time. In other embodiments, the tensioning element may be permanent. In some embodiments, at least one portion of the tensioning element may be modified after placement such as by trimming an excess portion of one end of the tensioning element.

In some embodiments, the tensioning element may, especially when deployed submucosally using an absorbable polymer, induce a remodeling response in a target tissue. In some embodiments where nasal cartilage is a target tissue, this remodeling response may include the formation of a pseudocapsule that functions to first protect against pressure necrosis, as is reported after the implantation of some non-absorbable implants, and second enable chondrocyte nutrition. The pseudocapsule may, from a histological view, enable the cartilage underneath the tensioning element to remain completely unchanged. In some embodiments, the tensioning element may also induce the recruitment or formation of new chondroblasts and the deposition of new cartilage at the border of the pseudocapsule or tensioning element. In some embodiments, this remodeling process may be optimized to occur within 5-25 weeks. In some embodiments, the process may be further optimized such that chondroblasts and new cartilage growth along the border of the cartilage defect occurs after about five weeks and absorption of the tensioning element is appreciable after about eight to twelve weeks, with complete absorption within about twenty five weeks.

Figure 7:
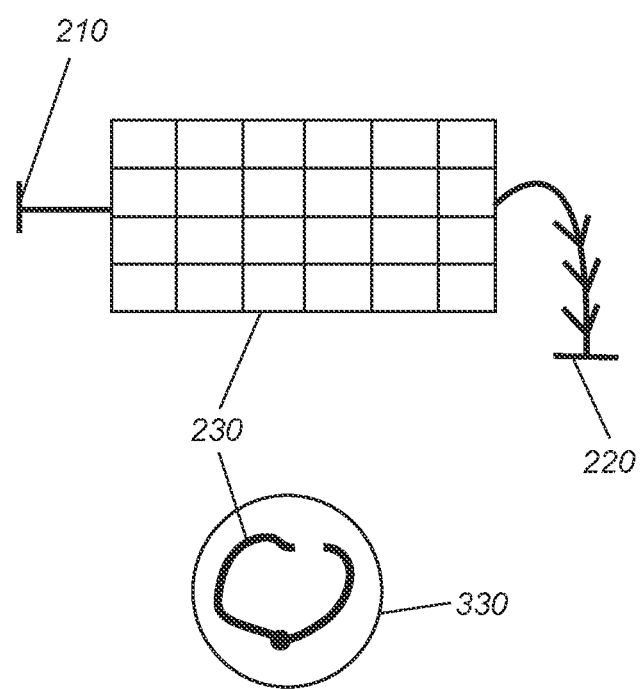
FIG. 7 depicts a further exemplary tensioning element including a plurality of migration prevention elements and a mesh-like force distributing region.

As shown in FIG. 7, in some embodiments the force distributing region (230) may have a solid, mesh-like, or other suitable configuration such that the force distributing region is able to be compressed in a delivery element. For example, as shown in FIG. 7, the force distributing region (230) may optionally be configured to be rolled in an elongated shaft (330) of a delivery tool.

Figure 8:
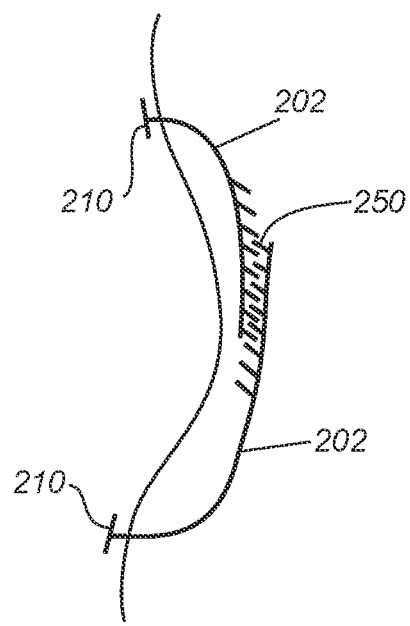
FIG. 8 depicts yet another exemplary tensioning element including multiple components that interact in an adjustable manner to apply tension to tissues.

As shown in FIG. 8, in some embodiments, the tensioning element (200) may be configured as at least two multiple components (202) that may contain an interaction mechanism (250). The interaction mechanism primarily functions to secure the multiple components with relative position in an adjustable manner. In some embodiments, the interaction mechanism may be configured as a catching mechanism, such as a zipper, ring grip, cinch, clasp, webbing buckle, or pressure gripping. In some embodiments, the interaction mechanism may be configured as a locking mechanism such as a button, tongue buckle, or snap buckle. In some embodiments, the interaction mechanism may be configured as a pinning mechanism, adhesive mechanism, or in any other suitable configuration for resisting the relative motion of the multiple components. In some embodiments, the interaction mechanism may set permanently. In some embodiments, the interaction mechanism may be adjustable over time or at different times. In some embodiments, the multiple components are secured on the non-interacting end with a position securing or movement resisting element or elements. In some embodiments, the multiple components are connected as one tensioning element, but the relative position of each component may be adjustable and securable via an interaction mechanism.

In some embodiments, the tensioning element may be fitted with an energy delivery element, such as one or more permanent or temporary electrodes, heating elements, or other energy delivery mechanism that allow the tensioning element to deliver energy to the nasal tissue. The energy delivery mechanism may be used to augment reshaping or remodeling of the nasal tissue by application of heat, electric current, or any suitable form of energy. In some embodiments, the energy delivery mechanism may be removed after energy is applied. In some embodiments, the energy delivery mechanism may be implanted with the tensioning element. In some embodiments, the energy delivery mechanism may be bioabsorbable or biodegradable. In some embodiments, the energy delivery mechanism is attached directly to the tensioning element. In some embodiments, the energy delivery mechanism is situated adjacent to the tensioning element.

In some embodiments, the tensioning element may be configured with a fluid delivery mechanism such as a conduit, channel, or other mechanism for suitable delivery of fluid to nasal tissue, as previously described. This fluid delivery mechanism may allow for the passage of fluid to achieve a therapeutic or physiologic effect. For example, the fluid delivery mechanism may be used to deliver a cold gas or liquid for the purposes of cryotherapy.

In some embodiments, the tensioning element may induce tissue remodeling. In some embodiments, the tensioning element may maintain a shape of a nasal tissue for a period of time sufficient to induce tissue remodeling. In other embodiments, the tensioning element may maintain a force acting upon a nasal tissue for a period of time sufficient to induce tissue remodeling.

Figure 9:
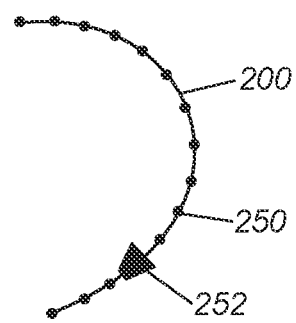
FIG. 9 depicts an exemplary tensioning element according to another variation including an adjustable securing element.

As shown in FIG. 9, the tensioning element (200) may optionally have an adjustable securing element (252) that can alter the tension, pressure, or position of the tensioning element. Optionally, multiple adjustable securing elements may be provided on the tensioning element (not shown), e.g., initially adjacent each end of the tensioning element. In some embodiments, the adjustable securing element uses a ball-in-cone ratcheting mechanism. In one embodiment, the tensioning element has one or more eminencies, protrusions, sphere, or tuberosities (250) positioned along its length. These protrusions are designed to pass first through a dilated end of the adjustable securing element (252) and then through a narrowed end of an adjustable securing element. The protrusion (250) and adjustable securing element (252) interaction may allow the tensioning element to be gradually tightened or shortened in a one-way fashion so as to prevent retraction and/or to augment pressure application of the tensioning element. In one embodiment, these protrusions are spherical in shape. In another embodiment, the adjustable securing element (252) may have a reversible configuration to allow the protrusions (250) to be retracted back through adjustable securing element. The protrusions (250) and adjustable securing element (252) may be made of a same or different material as the tensioning element (200).

Figure 10:
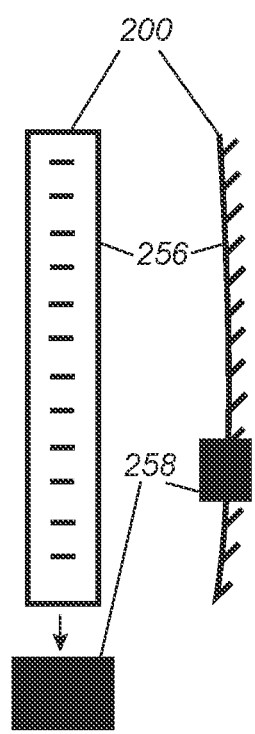
FIG. 10 depicts yet another exemplary tensioning element where the adjustable securing element interacts with ribs or fins positioned along the length of the tensioning element.
Figure 11:
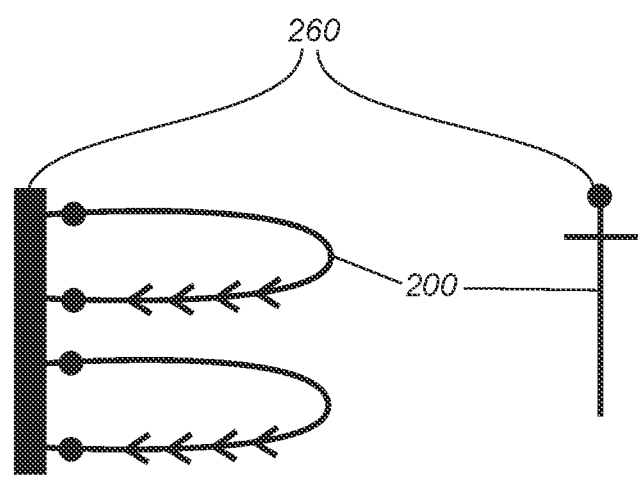
FIG. 11 shows a system according to another variation where multiple tensioning elements are held together with a detachable element.

As shown in FIG. 10, in some embodiments, the adjustable securing element (258) interacts with ribs or fins (256) positioned along the length of the tensioning element and are designed to be advanced through the adjustable securing element (258) in a one-way fashion. In another embodiment, the adjustable securing element (258) may be altered to allow the tensioning element to be pulled in the reverse direction. The ribs (256) and adjustable securing element (258) may be made of a same or different material as the tensioning element (200). The ribs may be oriented parallel, orthogonal, or oblique with respect to the longitudinal axis of the tensioning element. The tensioning element and adjustable securing element may be deployed by the same or different device.

In some embodiments, multiple tensioning elements may be held together with a detachable element (260). The detachable element (260) is designed to allow a plurality of repeating tensioning elements to be held together for loading into a delivery device. The detachable element may be made of a polymer, metal, composite, alloy, or any suitable material to allow the intended functionality. In another embodiment, multiple tensioning elements may be held together in a cartridge. In another embodiment, multiple tensioning elements may be held together in a sheet or any other configuration that allows a plurality of tensioning elements to be delivered either individually or simultaneously via the deployment mechanism of a delivery device.

Figure 12:
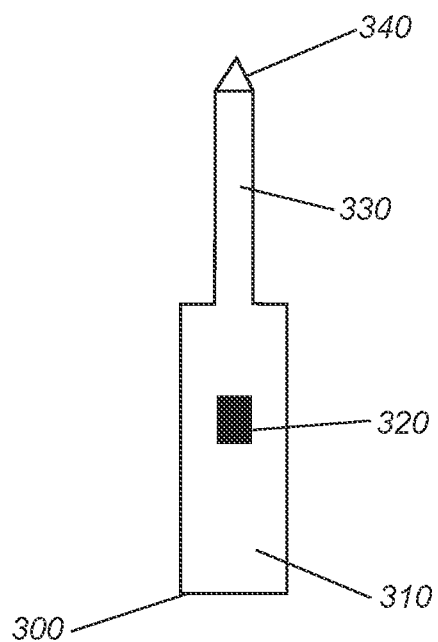
FIGS. 12 and 13 depict exemplary devices for delivering tensioning elements.
Figure 13:
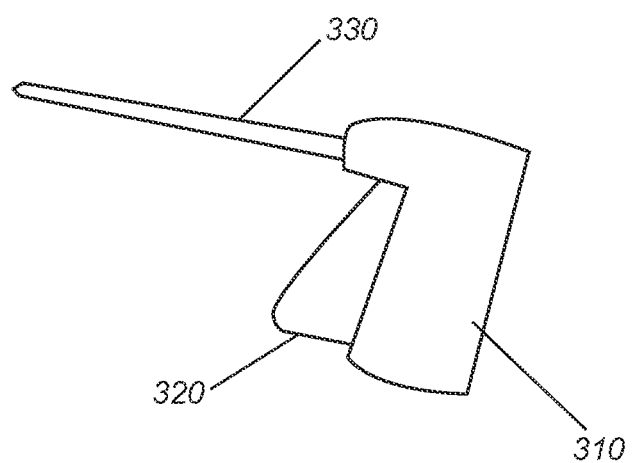

Turning to FIGS. 12 and 13, an exemplary embodiment of a delivery device (300) is shown that is configured to deliver a tensioning element for altering the shape of a nasal tissue includes a body (310), at least one action mechanism (320), an elongated shaft (330), and an optional tip (340). In some embodiments, the deployment device (300) may have a body (320) of an elongated or "pistol grip" shape (FIG. 13). In some embodiments, the at least one action mechanism (320) may be on the anterior, posterior, superior, inferior, or lateral aspect of the deployment device. The action mechanism may be a trigger, button, lever, arm or any alternative suitable conformation in order to achieve a desired function. In some embodiments, the optional tip (340) may be blunt or sharp. In some embodiments, the tip (340) may be parallel with or oriented at an angle to the elongated shaft (330). In some embodiments, the elongated shaft (330) and/or tip (340) houses a tensioning element and placement mechanism to deliver the tensioning element through, on, or adjacent to the nasal tissue.

Figure 14:
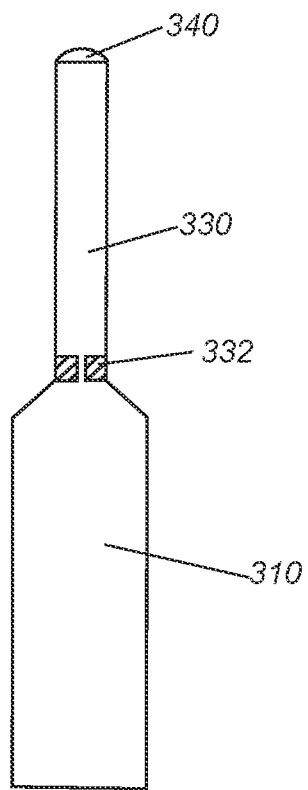
FIG. 14 depicts an exemplary delivery device according to another embodiment that includes an attachment site on the delivery device shaft for attachment to, or removal from, the body of the device.

As shown in FIG. 14, in some embodiments, the elongated shaft (330) may include an attachment site (332) for attachment to, or removal from, the body of the device (310). In such embodiments, the device may be configured to utilize various attachments using the same attachment site on the body of the device. In some embodiments, this will allow the elongated shaft to be replaced with another identical elongated shaft with the same configuration. For example, in the case where the elongated shaft includes only one tensioning element, it may be necessary to use multiple elongated shafts throughout the same procedure. Different attachments may be configured with the same primary function and different sizes and shapes or may be configured with alternate functions. In some embodiments, the body of the device may be configured with multiple attachment sites.

In some embodiments, the delivery device may be configured to allow for determining the extent of tissue shape alteration. For example, the extent of nasal septal deviation correction. In one embodiment, the extent of shape change is determined by visual inspection of the nasal airway diameter. In another embodiment, the delivery device is configured to measure a force. For example, the delivery device may be configured to measure tension along the length of the tensioning element.

Figure 15:
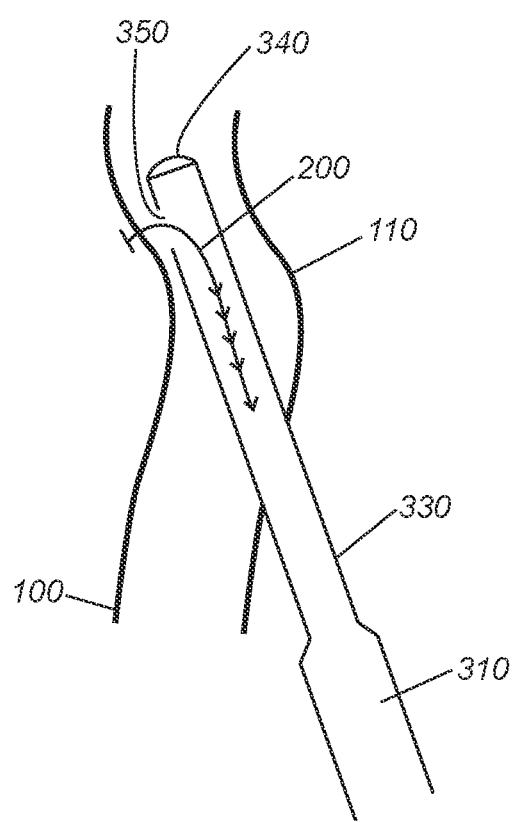
FIG. 15 depicts an exemplary delivery device including a blunt tip and an opening on the side of the delivery device shaft for lateral or orthogonal deployment of a tensioning element relative to the elongated shaft.

As shown in FIG. 15, some embodiments of a delivery device for altering the shape of a nasal tissue may include a blunted tip (340) of an elongated shaft (330). In this embodiment, the elongated shaft may optionally house at least one tensioning element (200) to be used to alter the shape of the nasal tissue. The elongated shaft may have an optional opening (350) that is on the side of the elongated shaft allowing for lateral or orthogonal deployment of the tensioning element relative to the elongated shaft. In another embodiment, an opening (350) for delivery of a tensioning element may be located at the distal end of the elongated shaft at its tip (340) to allow for parallel or oblique delivery of the tensioning element relative to the shaft. In some embodiments, the delivery device (300) may be configured to accept more than one tensioning element via a cartridge, sheet, or any other suitable configuration of a plurality of braces. In an embodiment where the delivery device is used for altering the shape of a nasal septum (100), the tip of the delivery device (340) may be inserted beneath the septal mucosa (110) and advanced to a desired position. In this case, the tip may contain a visualization element that can be used to track the position of the tip beneath the septal mucosa. Once at the desired site of placement, the delivery device may be activated to place at least one securing element of at least one tensioning element. In other cases, the delivery device may be positioned above the nasal septal mucosa before activation for placement of at least one securing element of at least one tensioning element.

Figure 16:
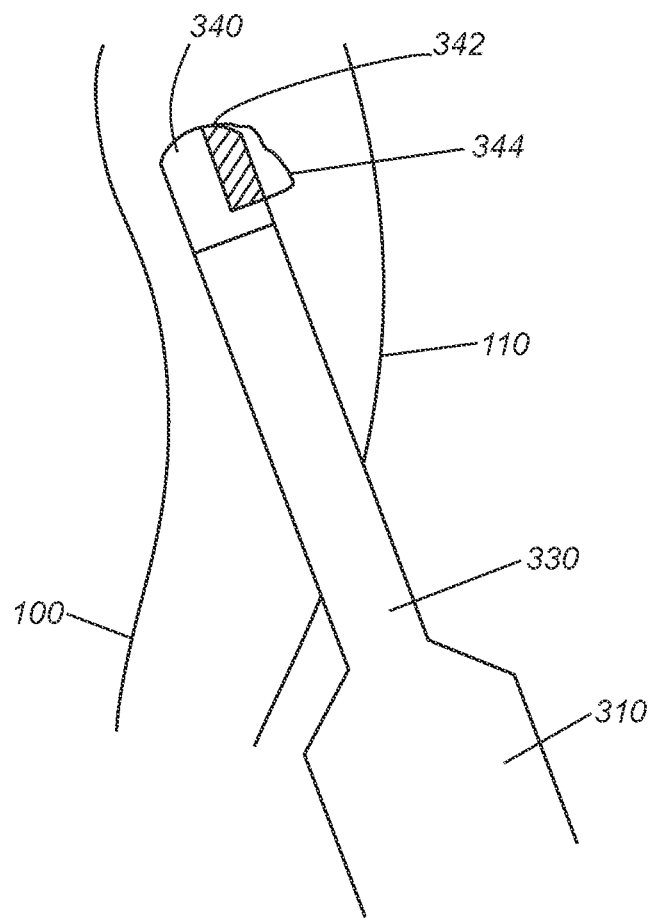
FIG. 16 depicts another exemplary delivery device including a visualization element at the tip of the device.

As shown in FIG. 16, some embodiments of a delivery device for altering the shape of a nasal tissue may include an optional visualization element (342) on the optional tip (340). The visualization element primarily functions to aid in positioning the device while it is beneath the nasal mucosa (110). The visualization element may be configured as an LED, a magnetic component, an electronic transmitter or receiver, or may be configured as any other material suitable for localization beneath the mucosa. In some embodiments, the tip of the delivery device may include a fin (344). The fin primarily functions to displace the overlying mucosa to aid in positioning the device while it is beneath the nasal mucosa (110). The fin may be configured to temporarily deploy or change shape to allow for transient displacement of the overlying mucosa. In some embodiments, the elongated shaft or tip of the delivery device may be adjustable in length. This may be accomplished via a telescoping mechanism, sliding mechanism, or any other suitable mechanism to alter the length of the elongated shaft or tip. In other embodiments the elongated shaft or tip may have an adjustable diameter. The elongated shaft or tip may also me malleable or shape adjustable. The elongated shaft or tip may also be able to rotate along its long axis. The elongated shaft or tip may also be fitted with an aspiration element to allow for suctioning of fluid. The elongated shaft or tip may also be fitted to hold or receive an endoscope. The elongated shaft or tip may also be fitted with a light to allow for enhanced visualization. The tip (340) may be of any suitable shape to allow for atraumatic maneuvering in the nasal airway and/or submucosal space. For example, the tip may be cylindrical or flat. It may alternatively have a non-symmetric configuration such as a shovel or scoop tip. In some embodiments, the tip may also be configured to include a cutting edge. The cutting edge may be configured to be retractable or fixed and can be used to facilitate introduction of the tip into a nasal tissue, separation of nasal tissues, or otherwise assist with positioning of the device.

Figure 17:
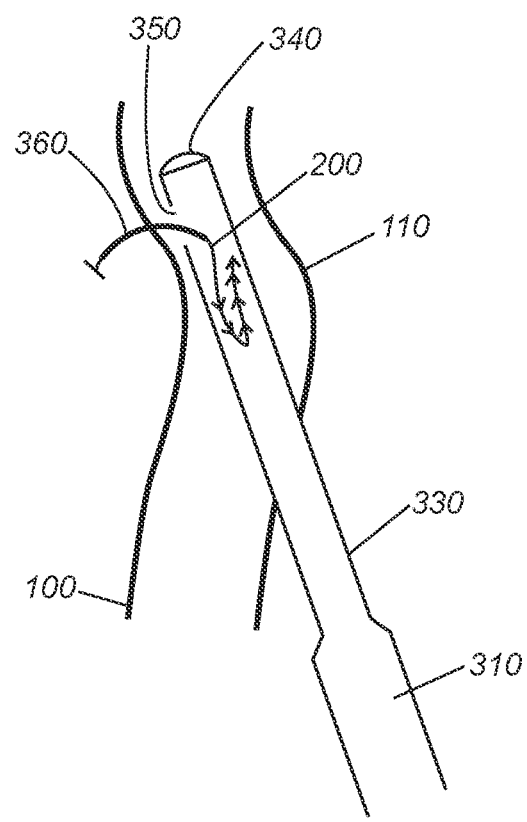
FIG. 17 depicts yet another exemplary delivery device including a placement mechanism to assist with deployment of a tensioning element into tissue.

As shown in FIG. 17, some embodiments of a delivery device for altering the shape of a nasal tissue have a placement mechanism (360) (also known as a delivery or deployment mechanism) that enables placement of a tensioning element. The placement mechanism may optionally be designed to extend out of an opening in the elongated shaft (350) to pierce or otherwise traverse the nasal tissue. Such an opening may be placed at the distal end of the tip or on the side of the elongated shaft or in any other suitable position to allow for optimal placement of the tensioning element. The placement mechanism (360) may be activated by an action mechanism located on the delivery device (310). In some embodiments, the placement mechanism may be pointed or sharp. It some embodiments, the placement mechanism may have an arc or other suitable shape appropriate for the desired function of penetrating or crossing the nasal tissue. Optionally, the placement mechanism may be fitted with an energy delivery element to facilitate tissue penetration. Optionally, the placement mechanism (360) may have an inner cannula which houses a tensioning element (200). In other embodiments the tensioning element may otherwise be secured to the outer portion of the placement mechanism. Once activated, the placement mechanism (360) may eject or otherwise release a desired end of the tensioning element (200). Once deactivated by means of releasing its action mechanism, the placement mechanism (360) may retract back through the opening (350) and into the housing of the elongated shaft (330).

Figure 18:
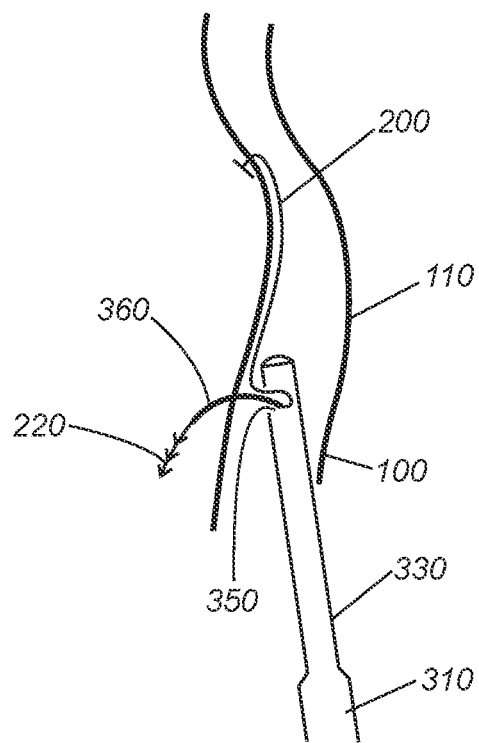
FIG. 18 depicts a further exemplary delivery device that places a first securing element at the distal end of a tensioning element, and a second securing element or migration prevention element at the proximal end of the tensioning element.

As shown in FIG. 18, one embodiment of the delivery device is configured with a placement mechanism (360) to allow for a first placement of a securing element (210) beneath the nasal septal mucosa (110) and across the nasal septal cartilage (100) at the distal end of the tensioning element (200) followed by a second placement of a securing element or migration prevention element (220) at the proximal end of the tensioning element. In some embodiments, the placement mechanism (360) has a reloading action such that it is able to capture the next desired aspect of the current or next tensioning element. In some embodiments, the placement mechanism (360) is designed to reload with an additional tensioning element fed from a cartridge, sheet, or other suitable configuration of a plurality of tensioning elements.

Figure 19:
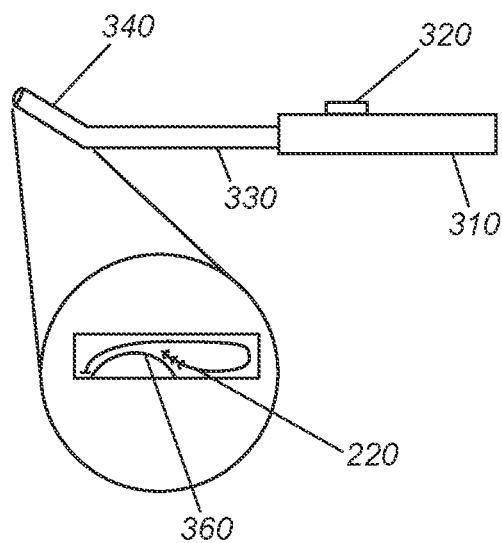
FIG. 19 depicts an exemplary delivery device including a retractable mechanism for deploying a tensioning element into tissue.

As shown in FIG. 19, one embodiment of a delivery device for altering the shape of a nasal tissue has a placement mechanism (360) that captures the first end of the tensioning element. An activation mechanism (320) may be used to protrude the placement mechanism (360) such that the placement mechanism penetrates or otherwise crosses the nasal tissue and subsequently ejects the first end of the tensioning element. Once deactivated by means of releasing the action mechanism, the placement mechanism (360) may retract back through the opening (350) and into the housing of the tip (340) and/or elongated shaft (330). In some embodiments, the placement mechanism will be designed to capture the second end (220) of the tensioning element such that it may be placed at a different location from the first end.

Figure 20:
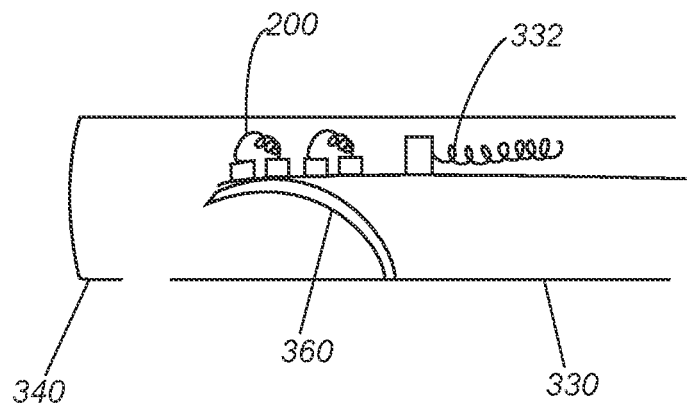
FIGS. 20 and 21 depict other exemplary delivery devices that include placement mechanisms having a reloading element.

As shown in FIG. 20, one embodiment of a delivery device for altering the shape of a nasal tissue has a placement mechanism (360) with a reloading element (332) that is capable of reloading the placement mechanism with additional ends of additional tensioning elements (200). This function allows the user to place multiple tensioning elements with a single device without having to insert additional tensioning elements into the device. After ejection of a first end of a tensioning element, the reloading mechanism (352) functions to load the second end of the current tensioning element or first end of the next tensioning element into the placement mechanism. The reloading mechanism may include a spring, push rod, or any suitable configuration to allow for the intended purpose.

Figure 21:
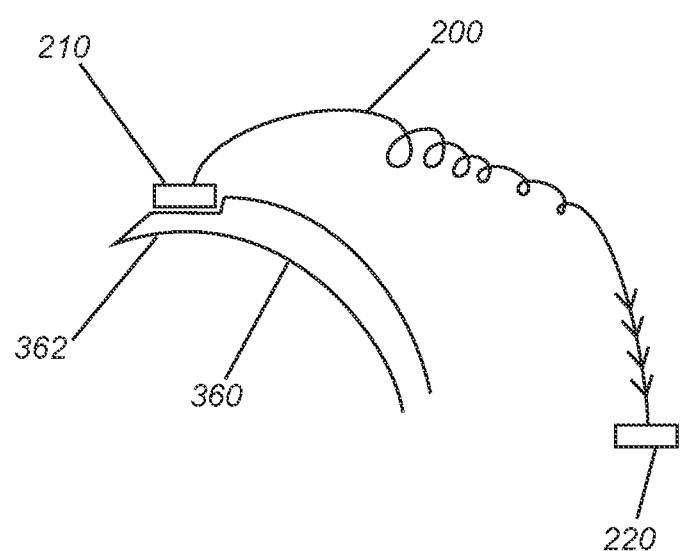

As shown in FIG. 21, one embodiment of the placement element (360) may have a receiving feature (362) that facilitates reloading of the next desired end of a tensioning element (210 or 220) by the reloading mechanism (332). This feature is designed to interact with either end of the tensioning element such that it temporarily secures the tensioning element onto the placement mechanism (360).

Figure 22:
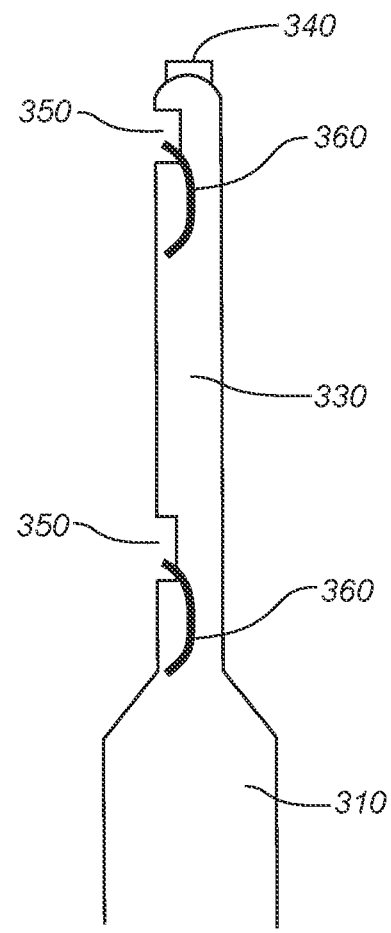
FIG. 22 depicts yet another exemplary delivery device including a plurality of placement mechanisms.

As shown in FIG. 22, in some embodiments of a delivery device for altering the shape of a nasal tissue, the device may be configured with multiple placement mechanisms (360). In such embodiments, the placement mechanisms may be configured to deploy multiple securing elements of one or more tensioning elements simultaneously or in sequence or may be configured to deploy multiple sections of a single tensioning element simultaneously or in sequence. In some embodiments, by utilizing multiple placement mechanisms, the device may be configured to apply the tensioning element into a final, secured position and may reduce the need to secure the tensioning element after its initial deployment. The optional multiple placement mechanisms may be located either in serial along the length of an elongated shaft or tip, or adjacent to each other at a specific length along the elongated shaft or tip.

Figure 23:
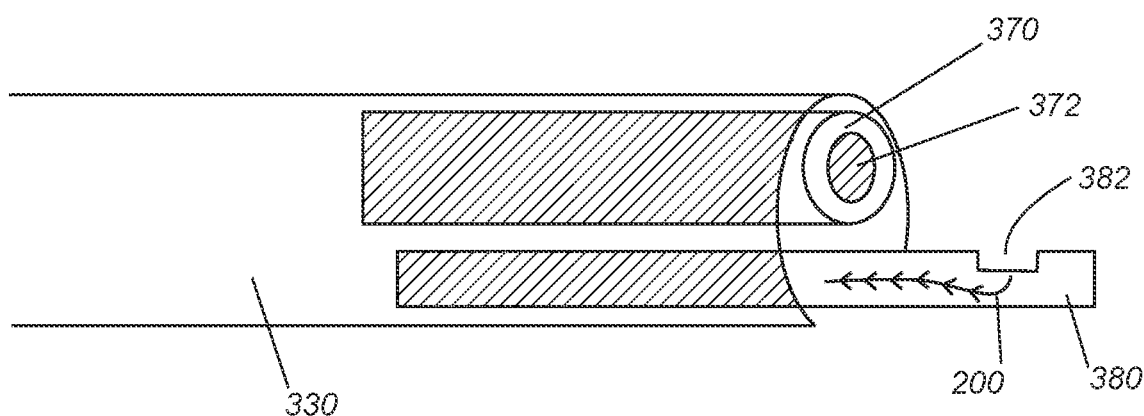
FIG. 23 depicts a further exemplary delivery device including a visualization element and an actuator arm that facilitates deployment of a tensioning element.

As shown in FIG. 23, some embodiments of a delivery device for altering the shape of a nasal tissue may include a visualization instrument (370) and/or an actuator arm (380) within the elongated shaft (330). The visualization element primarily functions to aid in visualization and may be configured as a disposable or reusable endoscope that is either flexible or rigid, a fiberoptic visualization system, a CCD, CMOS or other camera, or any another other suitable imaging or visualization modality. The visualization instrument may be configured with a wired connection or may be wireless. In some embodiments, the visualization instrument is included within the device; in other embodiments, the device is configured to house an external or separate visualization instrument of standard dimensions that may be inserted prior to use and removed afterwards. Optionally, the visualization instrument may include an adjustable lens (372) that is configured for visualization within the nasal tissue. In some embodiments, the delivery device may include an actuator arm (380) that may extend from within the elongated shaft (330). The actuator arm may extend parallel to the elongated shaft or may have joints or axes to enable additional degrees of positional freedom. The actuator arm may include an opening (382) to facilitate deployment of the tensioning element (200).

Figure 24:
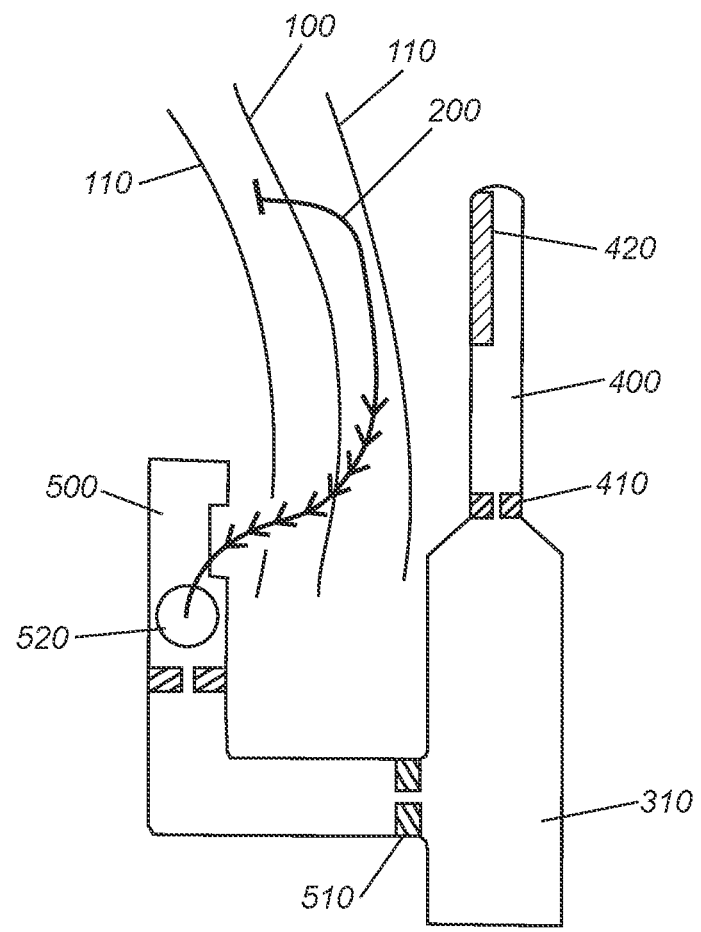
FIG. 24 depicts an exemplary delivery device according another embodiment that includes a mechanical element for manipulating tissue into a desired altered shape before securing the shape with a tensioning element, and a tightening mechanism for tightening the tensioning element from its initial deployment position to a final position.

As shown in FIG. 24, some embodiments of a delivery device for altering the shape of a nasal tissue may be configured to adjust the tensioning element (200). In some embodiments, the device may include a mechanical element (400) that primarily functions to mechanically manipulate the nasal tissue into a desired altered shape before securing the shape with the tensioning element. In some embodiments, the mechanical element may be attachable to the body of the device (310) via an attachment site (410). In some embodiments, the mechanical element may incorporate a sensing modality (420) to facilitate the alteration of a nasal tissue to a desired shape. In exemplary embodiments, the sensing modality or modalities may be selected from sensors including, but not limited to, pressure sensors, accelerometers, force meters, angular sensors, tilt sensors, distance sensors, or any other sensing modality suitable for assessing the shape of the nasal tissue. In some embodiments, the device may include a tightening mechanism (500). In some embodiments, the tightening mechanism is attached to the main body (310), via an attachment site (510). The tightening mechanism primarily functions to secure the tensioning element (200) from its initial deployment to a final position. Optionally, the tightening mechanism may include a locking mechanism (520) that functions to secure the tensioning element to the device so that it can be tightened in a controlled fashion. In other embodiments, the tightening mechanism has a sensor feedback system that adjusts the rate, strength, speed, or other measurable aspect of tightening relative to measurements taken from an applicable sensor. For example, in one embodiment, the tightening element may have a force or tension meter that modulates tightening based on output from this sensor. In some embodiments, tightening may cease once a certain threshold is detected by such a sensor.

Figure 25:
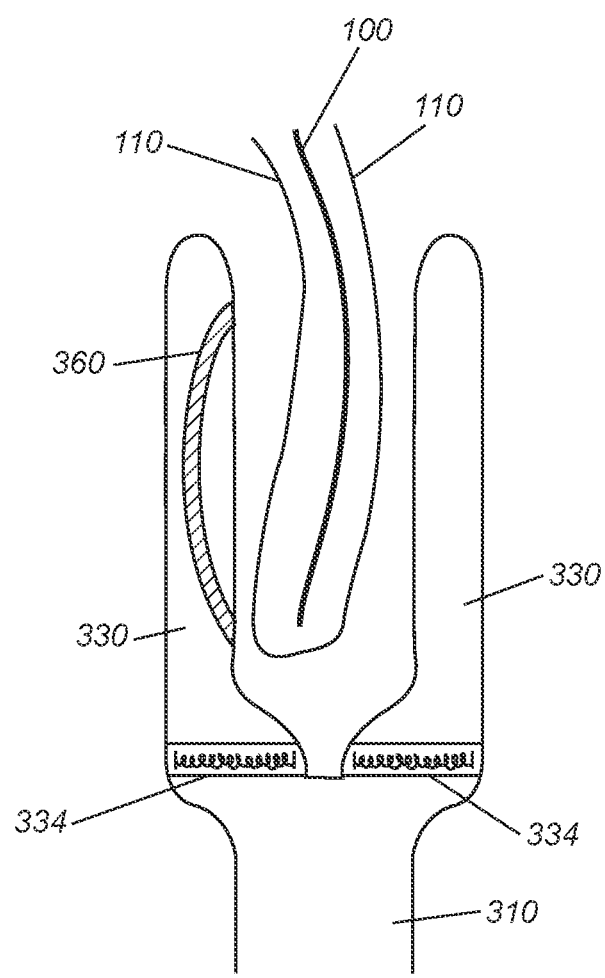
FIGS. 25 and 26 depict an exemplary device for delivering a tensioning element that alters the shape of the nasal septum.
Figure 26:
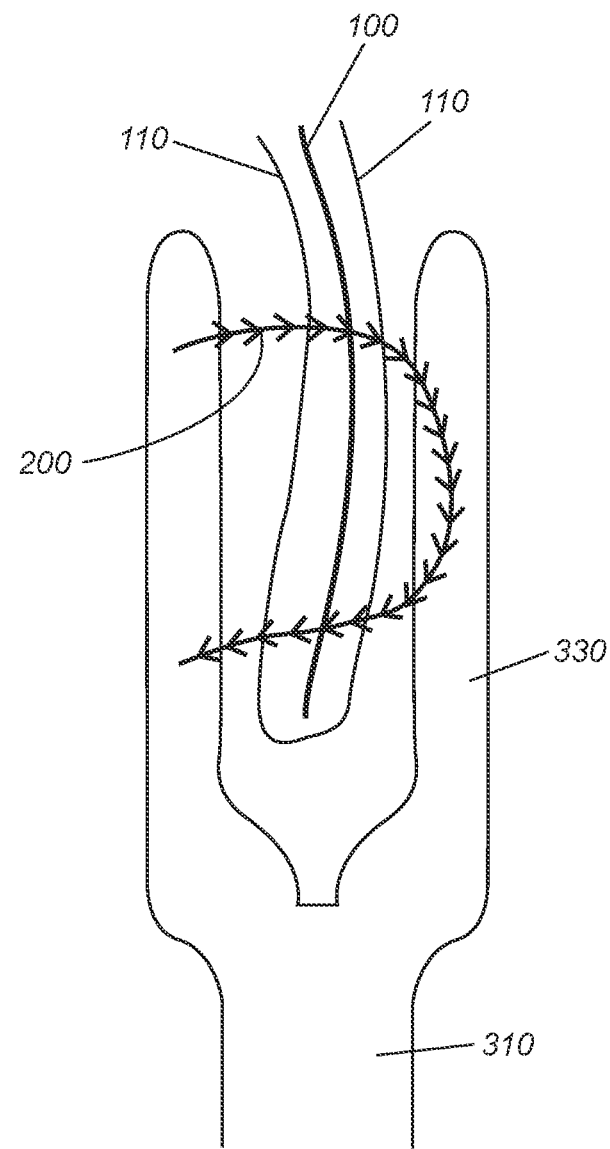

As shown in FIG. 25, some embodiments of a delivery device for altering the shape of a nasal tissue may be specifically configured for altering the nasal septum and may be configured to be deployed bilaterally, on either side of the septum. In some embodiments, the device may include multiple elongated shafts (330). In some embodiments, the relative position of the elongated shafts may be adjusted via one or more adjustable mechanisms (334). The adjustable mechanisms may function to manipulate the position of the elongated shafts in order to position the device for deployment of a brace across the nasal septal cartilage. The adjustable mechanisms may also function to apply force to the nasal septal cartilage or nasal bones to at least temporarily alter the shape before securing the brace. The device may include a deployment mechanism (360). In some embodiments, the deployment mechanism is configured to pass the brace between the elongated shafts and across the nasal septal cartilage, as shown in FIG. 26.

Figure 27:
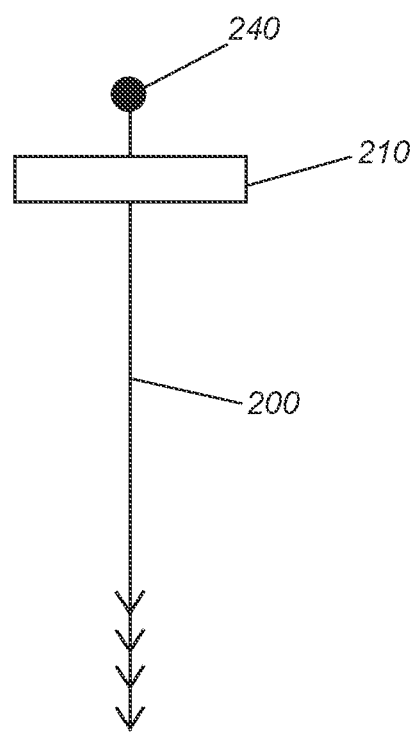
FIGS. 27 and 28 depict exemplary tensioning elements including components for securing the tensioning element in tissue.

As shown in FIG. 27, some embodiments of a tensioning element have an enlarged distal end (240) relative to the body of the tensioning element (200). The distal end may be any shape including but not limited to circular, spherical, hemispherical, rectangular, x-shaped, spiral, and the like. It may be designed to interface with a securing element (210); for example, as a ball-in-joint conformation. In some embodiments, the securing element moves in any plane relative to the tensioning element. In the particular embodiment shown in FIG. 27, the securing element is a rectangular structure that slides along the long axis of the tensioning element.

Figure 28:
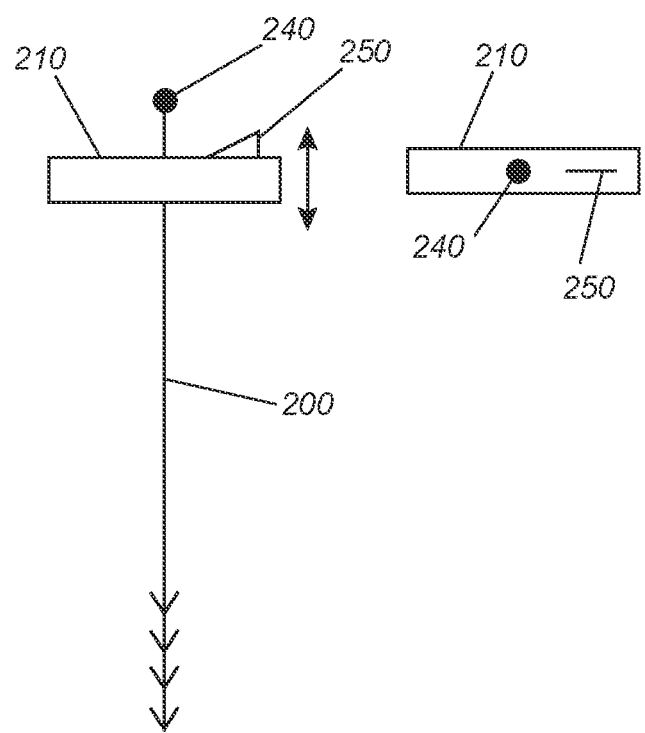

As shown in FIG. 28, in some embodiments the securing element may have a tissue interaction feature (250) that is designed to catch on tissue and cause the securing element to rotate, change position, or change shape. For example, shown in FIG. 28 is a fin feature that is triangular in shape such that when the securing feature is passed through tissue with the end of the securing feature opposite the end containing the fin, the fin is allowed to pass through the tissue but not back. In some embodiments, the securing element may be designed to interface with the placement mechanism of a delivery device such that the securing element is either passively or actively displaced from the placement mechanism of a delivery device.

Figure 29:
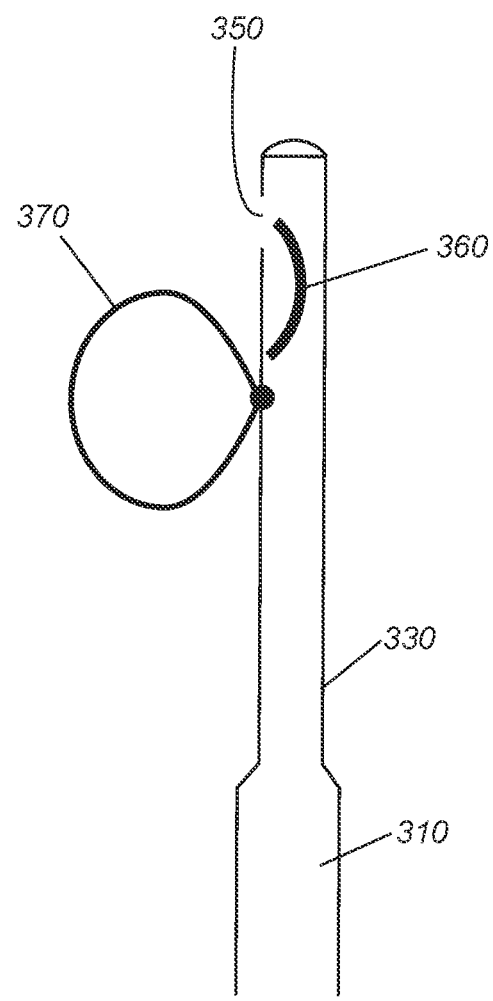
FIG. 29 depicts an exemplary delivery device including an expandable tissue displacement feature.

As shown in FIG. 29, some embodiments of a delivery device may include an expandable tissue displacement feature (370) that is designed to at least temporarily move tissue. One example of such an expandable tissue displacement feature would be an inflatable balloon designed to at least temporarily fracture or manipulate a nasal tissue into a desired shape.

Figure 30:
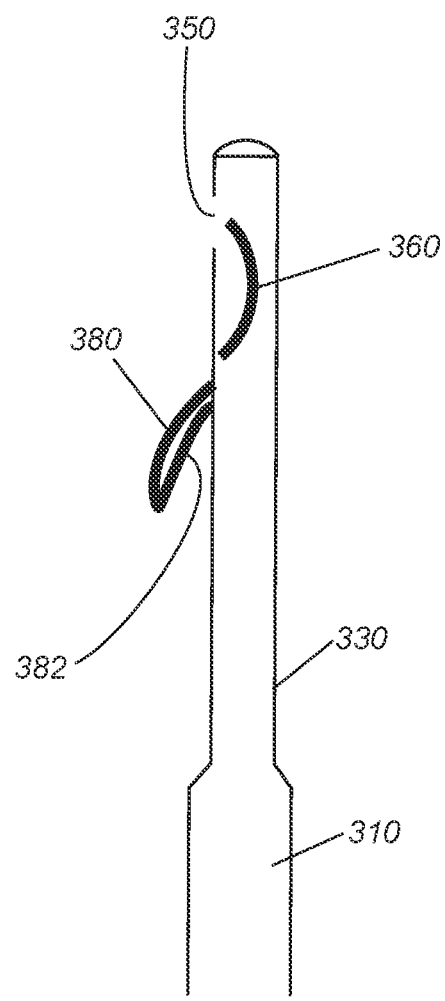
FIG. 30 depicts another exemplary delivery device including a tissue cutting feature.

As shown in FIG. 30, some embodiments of a delivery device may include a tissue cutting feature (382). In some embodiments, this tissue cutting feature may be housed within a deployable, expandable, adjustable, rigid, and/or flexible housing (380) such that the cutting feature does not engage with a tissue when the delivery device is moved in one direction but does engage with a tissue when the delivery device is moved in another direction.

Figure 31:
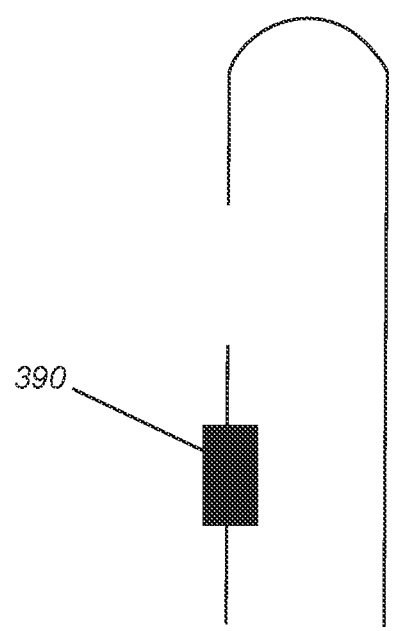
FIG. 31 depicts yet another exemplary delivery device including a tissue reduction feature.

As shown in FIG. 31, some embodiments of a delivery device include a tissue reduction feature (390). In one embodiment, the tissue reduction feature may be a motorized rotational burr designed to grind or file a tissue. The delivery device may include a housing for a battery or motor and may have a button or switch designed to turn the tissue reduction feature on or off.

Figure 32:
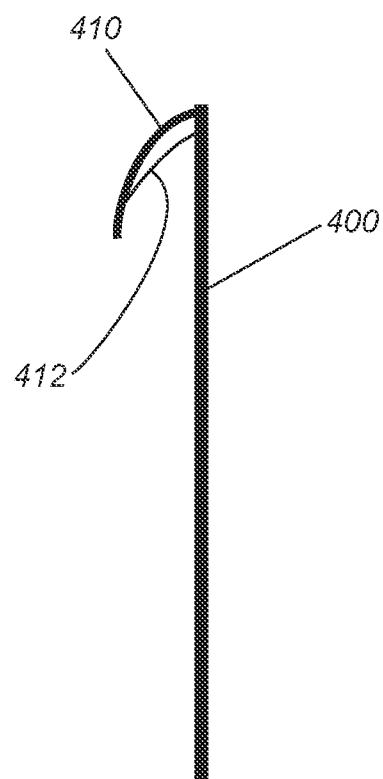
FIGS. 32 and 33 depict a further exemplary delivery device including a tissue cutting instrument that does not engage tissue when moved in a first direction but which engages tissue when moved in a second direction.
Figure 33:
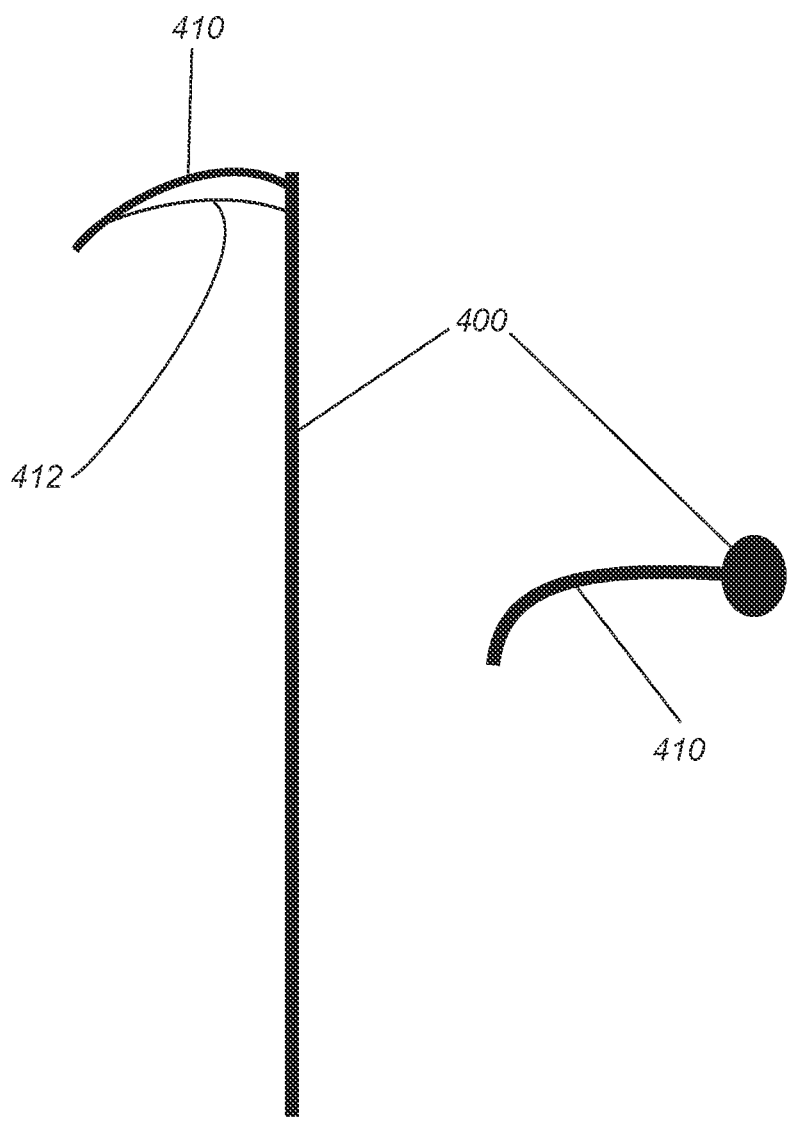

As shown in FIGS. 32 and 33, some embodiments of a system may include an accessory tissue cutting instrument (400). In some embodiments, this tissue cutting instrument includes a tissue cutting feature (412), which may be housed within a deployable, expandable, adjustable, rigid, or flexible housing (410) such that the cutting feature does not engage with a tissue when the cutting instrument is moved in one direction but does engage with a tissue when the cutting instrument is moved in another direction.

Figure 34:
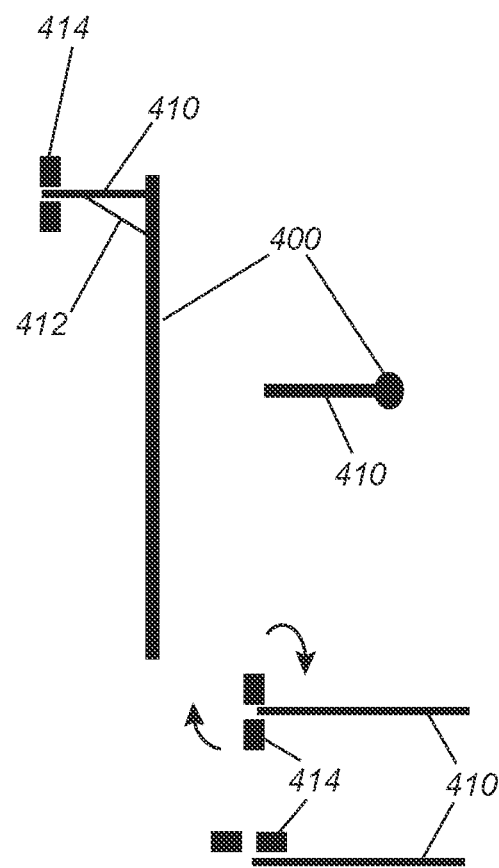
FIG. 34 depicts an exemplary accessory tissue cutting instrument including a head feature having first and second positions, and which allows puncturing through tissue in the first position but prevents pull back through the tissue when in the second position.

As shown in FIG. 34, some embodiments of an accessory tissue cutting instrument include a rotatable or expandable head feature (414) that changes from a first to a second position such that the instrument is able to puncture through a tissue in its first position but not pull back through when in its second position.

Figure 35:
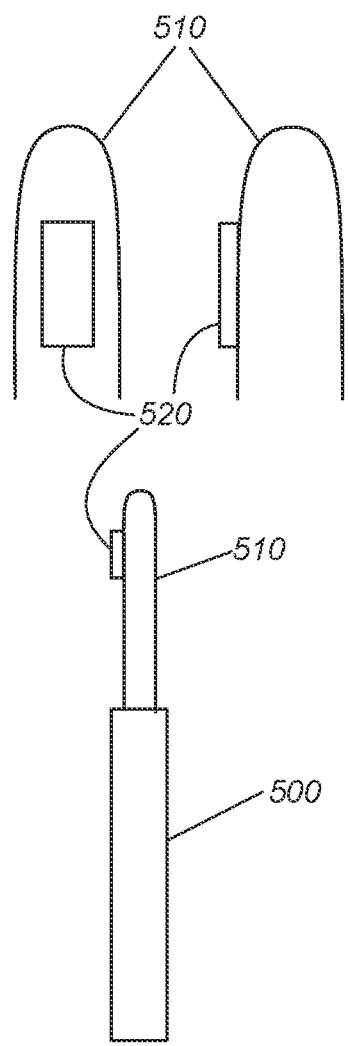
FIG. 35 depicts an exemplary accessory tissue reduction instrument designed to file or grind tissue.

As shown in FIG. 35, some embodiments of a system include an accessory tissue reduction instrument (500). In one embodiment, the tissue reduction instrument has a body, an elongate shaft (510), and a tissue reduction feature (520). In some embodiments, the tissue reduction feature includes ridges, ribs, or other features that allow the tissue reduction feature to file a tissue when manually moved. In other embodiments, the tissue reduction feature may be a motorized rotational burr designed to grind or file a tissue. The tissue reduction instrument may include housing for a battery or motor and may have a button or switch designed to turn the tissue reduction feature on or off.

Figure 36:
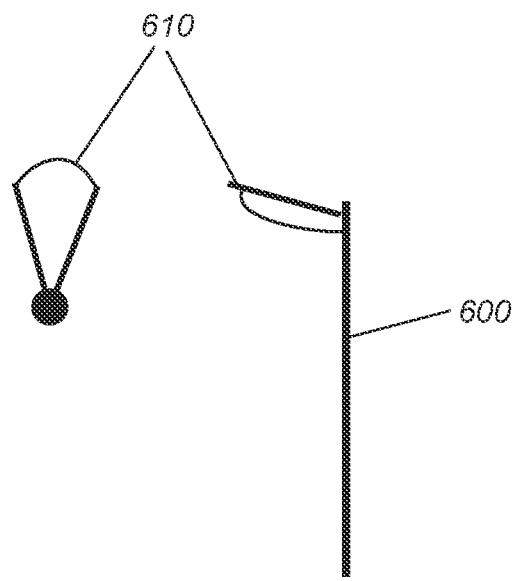
FIG. 36 depicts an exemplary accessory tissue displacement instrument.

As shown in FIG. 36, some embodiments of a system may include an accessory tissue displacement instrument (600). This instrument may have an elongate shaft and a head (610) that when moved, rotated, expanded, or otherwise activated is capable of at least temporarily displacing tissue. In one embodiment, this tissue displacement instrument may be designed in such a way that when the instrument is rotated about the axis of the elongate shaft the head also rotates such that the tissue is at least temporarily displaced away from the elongate shaft. In the case of nasal septal deviation secondary to deviation of the bony nasal septum, this may involve inward fracture of the bony septum so as to move it toward a more straightened conformation. In the case of nasal septal deviation, this instrument may be placed above or below the nasal septal mucosa.

Figure 37:
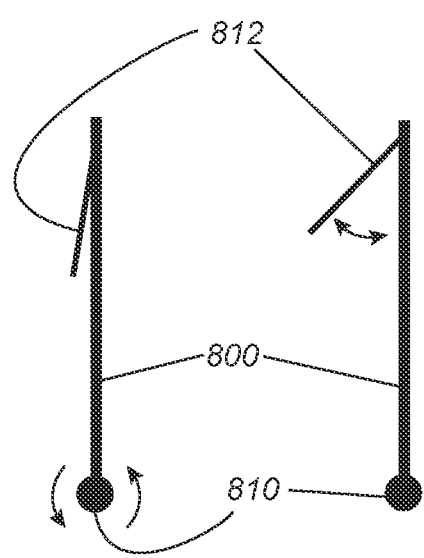
FIGS. 37 and 38 depict an accessory tissue displacement instrument according to another embodiment that displaces tissue upon changing from a first position to a second position.
Figure 38:
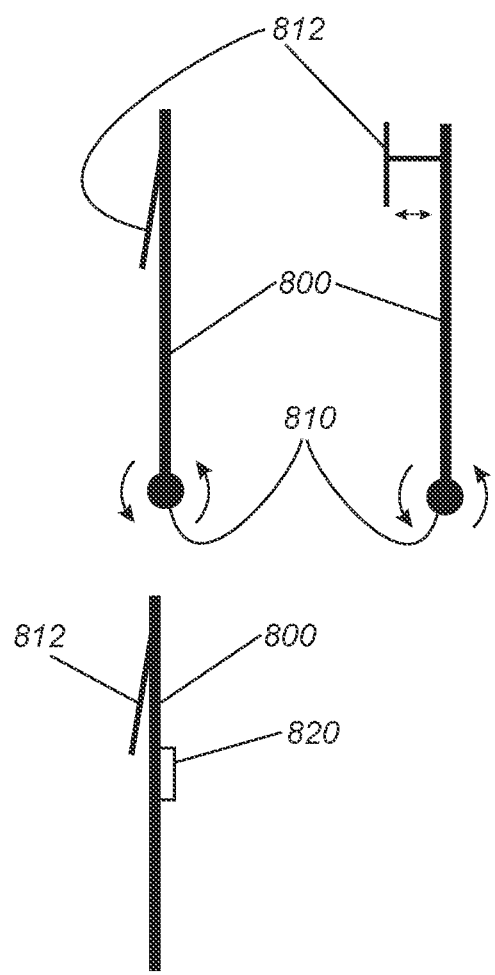

As shown in FIGS. 37 and 38, some embodiments of a system include a tissue displacement instrument with an expandable or deployable head (812) at one end of an elongate shaft (800) that, when deployed by an activation mechanism such as a switch, knob, button, inflation pump, or other suitable mechanism placed either at a second end of an elongate shaft (810) or along the body of an elongate shaft (820), changes from a first to a second position such that tissue is at least temporarily displaced.

Figure 39:
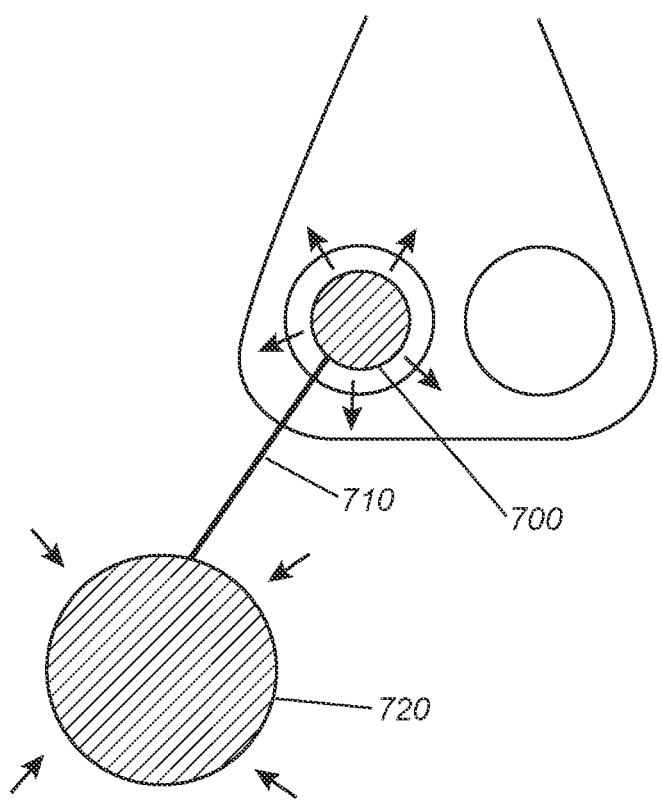
FIG. 39 depicts another exemplary tissue displacement instrument including an expandable element and an expansion activation element.

As shown in FIG. 39, some embodiments of a tissue displacement instrument include an internal balloon or expandable element (700) connected by a tube or elongated shaft (710) to an external expansion activation element (720).

Figure 40:
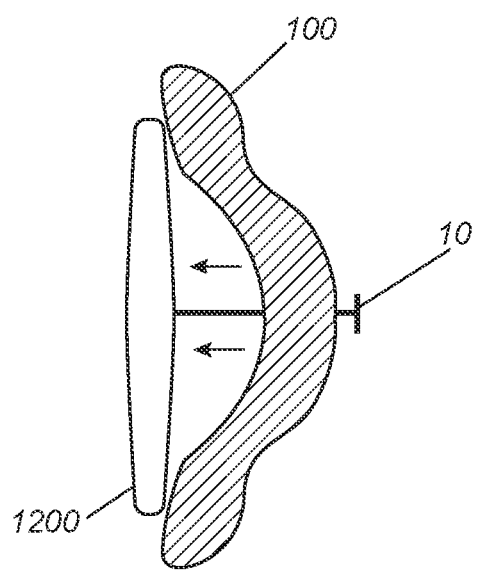
FIG. 40 depicts an exemplary tissue retention element for applying a force to tissue and holding the tissue in an altered shape.

As shown in FIG. 40, some embodiments of a system include a tissue retention element designed to hold a tissue into an altered shape (1000). This tissue retention element may also be known as a splint or stent. In some embodiments, this tissue retention element may be designed to straighten a deviated nasal septal cartilage (100). This tissue retention element may be placed above or below the mucosa. It may be placed on the concave or convex side of a deviation. It may include one or more tissue engagement features (10) that allow the tissue retention element to apply a force or remain connected to a tissue. The tissue retention element may be absorbable or nonabsorbable.

Figure 41:
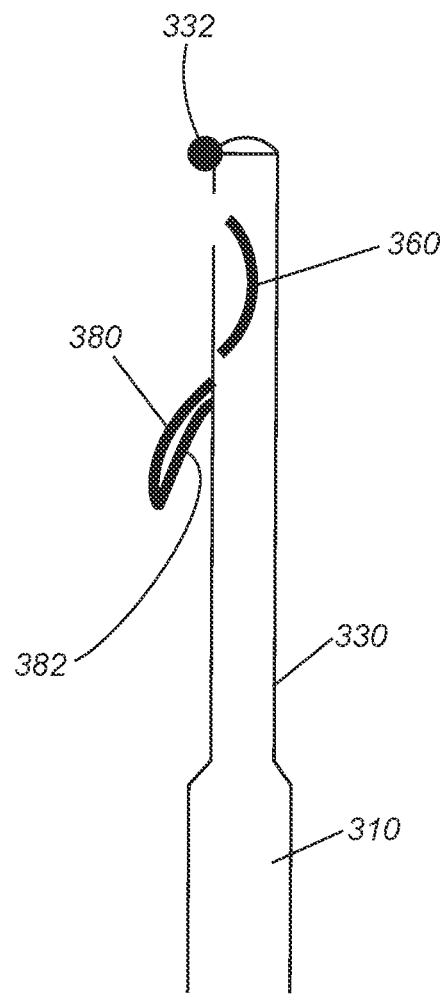
FIG. 41 depicts yet another exemplary delivery device including a tissue separation element.

As shown in FIG. 41, some embodiments of a delivery device include a tissue separation element (332) that allow the distal end of a delivery device to traverse within a tissue plane.

Figure 42:
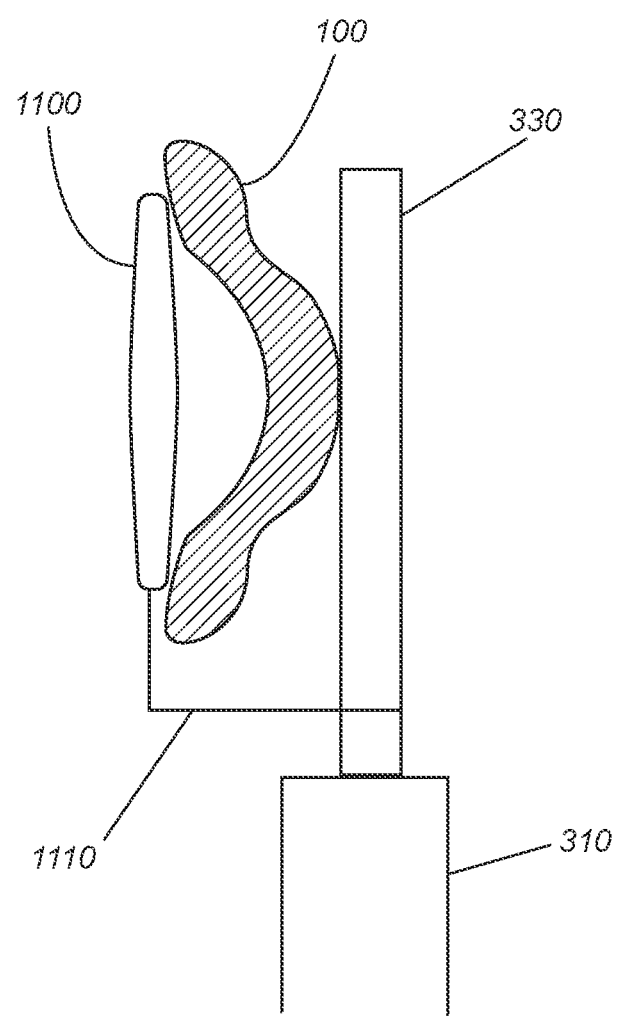
FIG. 42 depicts a further exemplary delivery device including an alignment feature for holding a tissue retention element in a position relative to the delivery device.

As shown in FIG. 42, some embodiments of a delivery device include an alignment feature (1110) that connects to either the elongate shaft (330) or body (310) of a delivery device such that it holds a tissue retention element in a position relative to the delivery device.

Methods

Methods for altering the shape of tissue structures of a subject are also described herein. The methods generally include deploying a shaping element or tensioning element into tissue, and manipulating the shaping element to apply a force to the tissue such that is alters the shape of the nasal tissue. The force may be a tensioning force. Various body tissues may be shaped using the tensioning force. Exemplary tissues include without limitation, nasal septal cartilage, lateral nasal cartilage, major or minor alar cartilages, alar fibrofatty tissue, nasal bone, and nasal turbinates.

The methods described herein may be used for treatment of nasal airway obstruction; treatment of a deviated nasal septum; straightening of a nasal septum; treatment of a thickened, deformed, or dislocated nasal septum; repair of nasal septal fracture; alteration of the shape of the nasal septum; treatment of nasal septal spurs or nasal bone spurs; alteration of the shape of the internal or external shape of the nose; treatment or alteration of structural deformity of a nasal cartilage other than the nasal septum; treatment of internal nasal valve collapse; or treatment of turbinate hypertrophy. The method may also be employed to treat or alleviate sleep apnea, nasal snoring, or may be configured for any other suitable alteration of nasal tissue or any combination of tissues.

When the shape of the nasal septal cartilage is to be altered, for example, to correct a deviated nasal septum, the method may include passing a suture, barbed suture, or shaping element, through the nasal septum, tightening the suture until the septum is straightened, and trimming the excess suture. In some embodiments, the method for adjusting the shape of a deviated septum may include applying between about 4.0 Newtons and about 40 Newtons of force to the nasal septum using the shaping element, including all values and sub-ranges therein. For example, about 4.0 Newtons, about 5 Newtons, about 10 Newtons, about 15 Newtons, about 20 Newtons, about 25 Newtons, about 30 Newtons, about 35 Newtons, or about 40 Newtons of force may be applied to the nasal septum. The same amount of force may be applied to other nasal tissues such as the lateral nasal cartilages, major or minor alar cartilages, alar fibrofatty tissue, nasal bone, and the nasal turbinates to alter their shape. In other embodiments, between about 12 Newtons and about 25 Newtons of force may be applied to the nasal septum using the shaping element.

In some embodiments, the method may employ a device that includes an elongate member comprising a proximal end, a distal end sized for introduction into the subject's body, and a lumen extending between the proximal end and a port in the distal end, and a shaping element. The shaping element may include a first end sized for introduction through the lumen to deploy the first end out the port to engage tissue adjacent the tissue structure, a second end opposite the first end, and one or more elements to maintain a force on the engaged tissue to alter the shape of the tissue structure.

Manipulating the shaping element may include manipulating a second end of the shaping element to apply a force to the tissue. In some embodiments, the second end of the shaping element may be secured to tissue adjacent the nasal airway after applying the force. Securing the second end may include directing the second end through tissue at a location spaced apart from the first end. In one embodiment, the first end may be secured to the tissue on one side of a deviated septum, and the second end is secured to the tissue on an opposite side of the deviated septum, and a force applied to alter the shape of the deviated septum. In another embodiment, the first end is secured to tissue distal to a deviated septum, wherein the second end may be secured to tissue proximal to the deviated septum, and a force applied to alter the shape of the deviated septum. The force applied by the shaping element is generally a tensioning force.

Alternatively, manipulating the shaping element may include engaging an intermediate region of the shaping element with tissue at a second location spaced apart from a first location to which the first end is secured, and applying a force to the shaping element between the first and second locations to alter the shape of the tissue between the first and second locations. One or more elements at the intermediate region may be engaged with the tissue at the second location to maintain the tension. Furthermore, engaging an intermediate region may include directing a second end of the shaping element through the tissue at the second location, and pulling the second end until the intermediate region engages the tissue at the second location. The intermediate region may include a plurality of migration prevention elements spaced apart from one another. Here the second end may be pulled until at least one of the migration elements passes through the tissue at the second location, thereby preventing the intermediate region from passing back through the tissue at the second location.

In some embodiments, manipulating the shaping element may further include adjusting a location of a securing element on the intermediate region with the tissue at the second location to maintain the tension. In other embodiments, the method further includes separating the second end of the shaping element from the intermediate region, for example, by cutting the shaping element adjacent the intermediate region to remove excess material from the shaping element.

In another embodiment, a method is provided for altering the shape of nasal tissue of a subject that includes inserting a distal end of a delivery device into a nasal airway of the subject, deploying a first end of a shaping element from the distal end into the nasal airway; securing the first end of the shaping element to tissue adjacent the nasal airway, manipulating the shaping element to alter a shape of the tissue, and removing the delivery device such that the shaping element at least temporarily maintains the altered shape of the tissue.

In a further embodiment, the method for altering the shape of nasal tissue of a subject includes deploying a first end of a shaping element into a nasal airway of the subject, securing the first end of the shaping element to tissue at a first location adjacent the nasal airway, manipulating the shaping element to alter a shape of the tissue, and securing the shaping element relative to tissue at a second location to maintain the altered shape of the tissue. Securing the shaping element at the second location may include securing a second end of the shaping element at the second location. In one embodiment, securing the shaping element at the second location includes securing one or more migration prevention elements on the shaping element at the second location. In another embodiment, the method further includes removing excess material of the shaping element once the one or more migration prevention elements are secured at the second location. In a further embodiment, the second location may be located closer to the nasal ostium than the first location.

Some methods for altering the shape of nasal tissue of a subject include introducing an anchor into a nasal airway of the subject, securing the anchor at a first location to a nasal septum of the subject, introducing a first end of a shaping element into a nasal airway of the subject, securing the first end of the shaping element to the anchor; manipulating the shaping element to alter a shape of the tissue, and securing the shaping element relative to tissue at a second location to maintain the altered shape of the tissue. The anchor may be introduced into a first nasal airway of the subject and secured by directing the anchor through the nasal septum at partially into a second nasal airway of the subject, and the first end of the shaping element may be introduced into the second nasal airway and secured to a portion of the anchor extending into the second nasal airway. In one embodiment, the first end of the shaping element is introduced into the nasal airway submucosally before securing the first end to the anchor.

Other methods for altering the shape of nasal tissue of a subject may include inserting a distal end of a delivery device into a nasal airway of the subject, deploying a first end of a shaping element from the distal end into the nasal airway, securing the first end of the shaping element to tissue at a first location adjacent the nasal airway, and removing the delivery device such that the shaping element extends from nasal airway. A needle coupled to a second end of the shaping element may then be inserted into the nasal airway, and the shaping element manipulated to alter a shape of the tissue. Securing the second end at a second location adjacent the nasal airway may temporarily maintain the altered shape of the tissue.

In some methods, shaping of nasal tissue may be accomplished using a shaping element or a tensioning element fitted with an energy delivery element. For example, one or more permanent or temporary electrodes, heating elements, or other energy delivery mechanism that allows the tensioning element to deliver energy to the nasal tissue may be included with the shaping element. The energy delivery mechanism may be used to augment reshaping or remodeling of the nasal tissue by application of heat, electric current, or any suitable form of energy. In some embodiments, the energy delivery mechanism may be removed after energy is applied. In some embodiments, the energy delivery mechanism may be implanted with the tensioning element. In some embodiments, the energy delivery mechanism may be bioabsorbable or biodegradable. In some embodiments, the energy delivery mechanism is attached directly to the tensioning element. In some embodiments, the energy delivery mechanism is situated adjacent to the tensioning element.

Fluids may also be delivered before, during, or after placement of the shaping element using a fluid delivery mechanism. The fluid may provide a therapeutic or physiologic effect. For example, the fluid may include a therapeutic agent, or a cold gas or liquid for the purposes of cryotherapy.

Exemplary Methods

As shown in FIG. 1, an exemplary method for altering the shape of a nasal tissue (100) includes deploying at least one tensioning or other shaping element (200) into the nasal airway, adjacent to a nasal tissue, and securing the tensioning element (200), such that the nasal tissue at least temporarily maintains an altered shape. The tensioning element can also be known as a brace, suture, graft, buttress, implant, or supporting element. The method may utilize one tensioning element or multiple tensioning elements arranged in a parallel or non-parallel fashion. In some embodiments, securing the tensioning element may allow for the application of force to the nasal tissue that is configured to at least temporarily allow the nasal tissue to maintain an altered shape. In some embodiments, the force may be a tension force. In some embodiments, securing the tensioning element may involve fixing a portion of the tensioning element through the target nasal tissue or through another nasal tissue. In some embodiments, the tissue through which the tensioning element is secured is cartilage, bone, any semi-rigid tissue, or any combination thereof. The method may be configured to adjust the shape of a nasal tissue to a final state in one application or may be configured with an adjustable tensioning element that allows adjustments to the force or shape to be made over time. The method may also be configured to utilize tensioning elements deployed at varying time points to alter the shape of a nasal tissue sequentially.

In some embodiments, the method may involve applying an external force to alter the shape of the nasal tissue before or during deployment of the tensioning device. In some embodiments, application of external force may be accomplished by means of a force applying element such as a nasal speculum, spreader, suture passer, forceps, or other tool or device suitable for manipulating the nasal tissue. In some embodiments, the force may be applied transmucosally or transcutaneously. In some embodiments, the method may involve applying an external force to alter the shape of the nasal tissue after initial deployment of the tensioning element but before final securing the tensioning element. In some embodiments, the method may involve applying an external force to alter the shape of the nasal tissue before or after deployment of the tensioning element.

In some embodiments, the method may be configured to be suitable for use in a medical clinic or office. In some embodiments, the method may be configured to be suitable for use in an otolaryngology clinic or office. In some embodiments, the method may be configured to be suitable for use in a surgical center or setting. In some embodiments, the method may be configured to include the use of an analgesic. In some embodiments, the method may be configured to include the use of anesthetic. In some embodiments, the method may be configured to include the use of supporting elements, which can also be known as splints. In some embodiments, the method may be configured to include elevating the nasal mucosa away from the target tissue by means of an instrument, balloon, or other method of mucosal elevation. In some embodiments, the method may be configured to include the use of a scope or other means of visualization. The methods described herein may be configured and/or adapted for one or more of treatment of nasal airway obstruction; treatment of a deviated nasal septum; straightening of a nasal septum; treatment of a thickened, deformed, or dislocated nasal septum; repair of nasal septal fracture; alteration of the shape of the nasal septum; treatment of nasal septal spurs or nasal bone spurs; alteration of the shape of the internal or external shape of the nose; treatment or alteration of structural deformity of a nasal cartilage other than the nasal septum; treatment of internal nasal valve collapse; or treatment of turbinate hypertrophy. The method can also be configured and/or adapted for sleep apnea, nasal snoring, or may be configured for any other suitable alteration of nasal tissue or any combination of tissues.

In some embodiments, a method for altering the shape of a nasal tissue may also include inserting a delivery device into the nasal airway, deploying at least one tensioning element (200), securing the tensioning element, and removing the device such that the nasal tissue at least temporarily maintains an altered shape. For example, the delivery device may be inserted into the nasal airway, inserted beneath the nasal mucosa, or positioned in any other configuration suitable for facilitating the placement or deployment of the tensioning element. In some embodiments, some or all of the delivery device may be disposable. In some embodiments, some or all of the delivery device may be reusable and may be configured to be suitable for sterilization.

Figure 2:
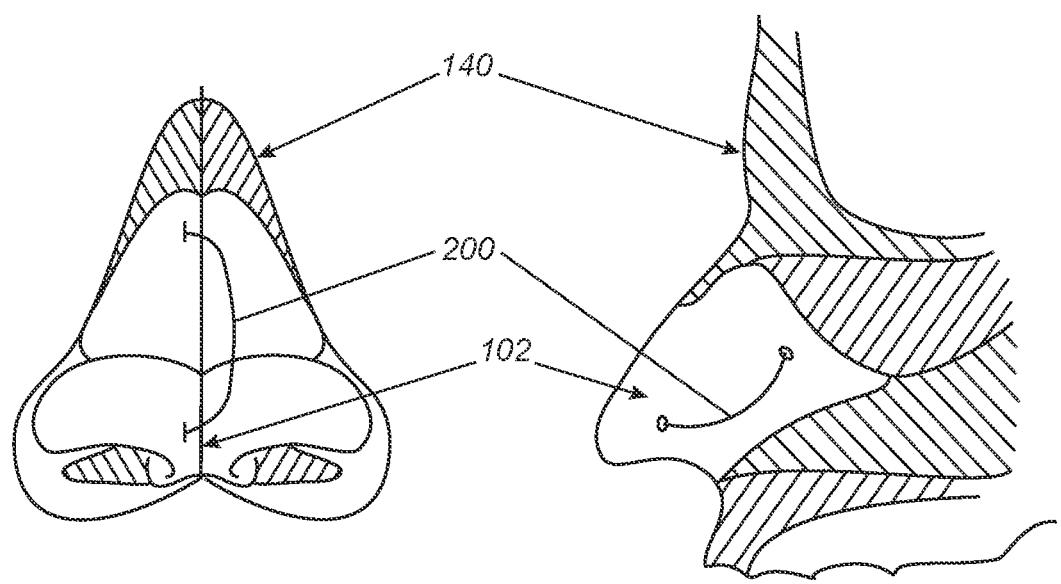
FIG. 2 depicts an exemplary method for shaping a nasal septal cartilage.

As shown in FIG. 2, a method for altering the shape of a nasal tissue may specifically be optimized for adjusting the shape of the nasal septal cartilage (102). The method may be configured to adjust the shape of a deviated septum of any kind, classification, or location, including, but not limited to, "C-shaped" deviations, "S-shaped" deviations, subluxation of septal cartilage, sagittal deviations, coronal deviations, deviations caused by bony deformation, cartilaginous deformation, ossified cartilage, dislocation of bone or cartilage, thickened or hypertrophied cartilage or bone, cartilaginous or bony spurs, trauma to bone or cartilage, or any other form of septal deviation or combination thereof. In some embodiments the method is used for correction of anterior caudal septal deviation. In some embodiments the method is used for altering the shape of the posterior septal cartilage. In some embodiments the method is used for correction of external nasal deformities involving the "L-strut," but may additionally or alternatively be used for any suitable applications, clinical, functional, cosmetic, or otherwise. In some embodiments, the tensioning element may be secured to or thorough cartilage. In some embodiments, the tensioning element may be secured to or through bone or any other suitable nasal tissue. In some embodiments the tensioning element may be placed on the convex side of the deviation. In some embodiments the tensioning element may be placed on the concave side of the deviation. In some embodiments where the method is configured for altering the shape of the nasal septal cartilage, the method may be configured as correction of a deviated nasal septum by means of passing suture or barbed suture through the nasal septum, tightening the suture until the septum is straightened, and trimming the excess suture. In some embodiments, the method configured for adjusting the shape of a deviated septum may be specifically optimized to provide between 4 and 40 Newtons of force. In some embodiments, the method may be further optimized to provide between 12 and 25 Newtons of force.

Figure 3:
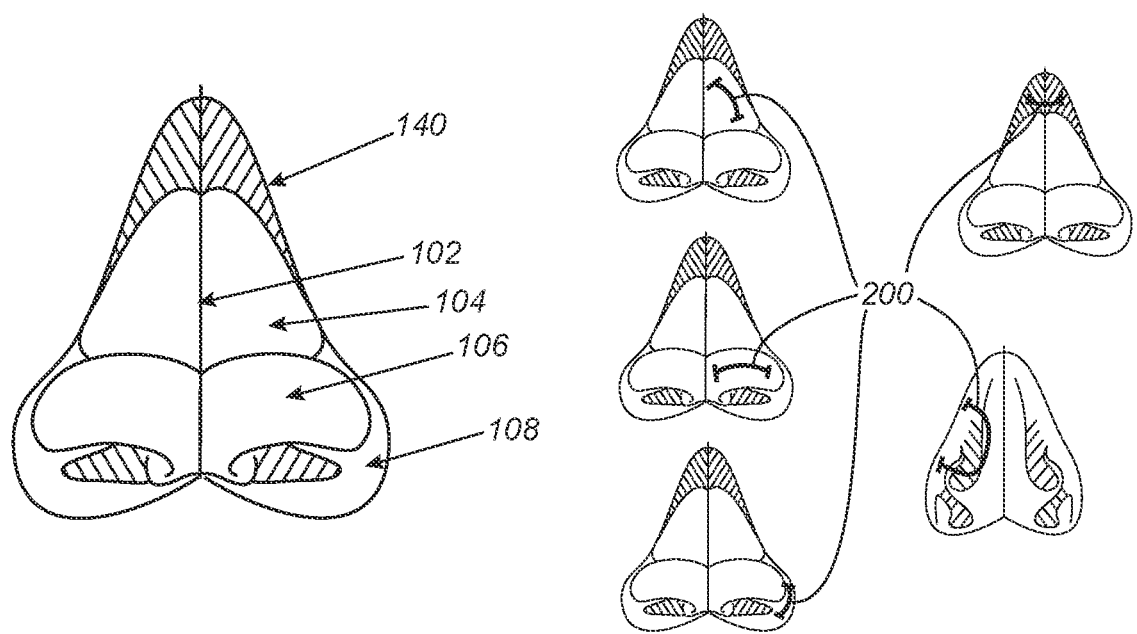
FIG. 3 depicts exemplary methods for shaping a lateral nasal cartilage, a major or minor alar cartilage, alar fibrofatty tissue, a nasal bone, and a nasal turbinate.

As shown in FIG. 3, a method for altering the shape of a nasal tissue may be specifically optimized for adjusting the shape of a nasal tissue other than the nasal septal cartilage (102). In some embodiments, the method may be configured to adjust the shape of the lateral nasal cartilage (104), the major or minor alar cartilage (106), the alar fibrofatty tissue (108), a nasal bone (140), a nasal turbinate (150), or any other suitable nasal tissue.

Figure 4:
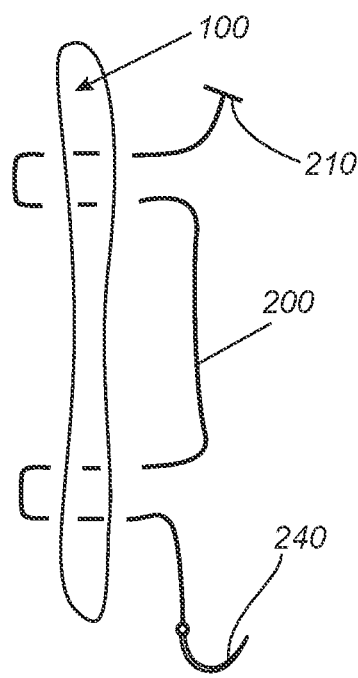
FIG. 4 depicts another exemplary tensioning element comprising a suture having a securing element at one end, and a needle at the other end.

As shown in FIG. 4, in some embodiments, the method may be configured to use suture or sutures as the tensioning element (200). In some embodiments, the tensioning element may be optionally be configured as barbed suture or sutures. The suture may be of any diameter, size, shape, length, or width. In some embodiments, the sutures may be arranged in a pattern to sufficiently alter the shape of a nasal tissue. The method may be configured for any number of suture passes or patterns. The suture may include a securing element (210) designed to prevent migration or translocation of the suture through the nasal tissue. The configuration may include a series of at least one vertical or horizontal-mattress-like sutures. In some embodiments, the suture may be placed and secured submucosally, transmucosally, or transcutaneously. In some embodiments, the suture may be introduced via a needle (240) attached to at least one end of the suture. The method may be configured to use a needle or needles that are straight, curved, flat, or otherwise shaped. The method may be configured to use a needle or needles that are attachable or detachable from the suture. The method may be configured to utilize a kit or packaged set of instruments, tools, or suture materials for placing and tensioning suture to alter the shape of a nasal tissue.

Figure 5:
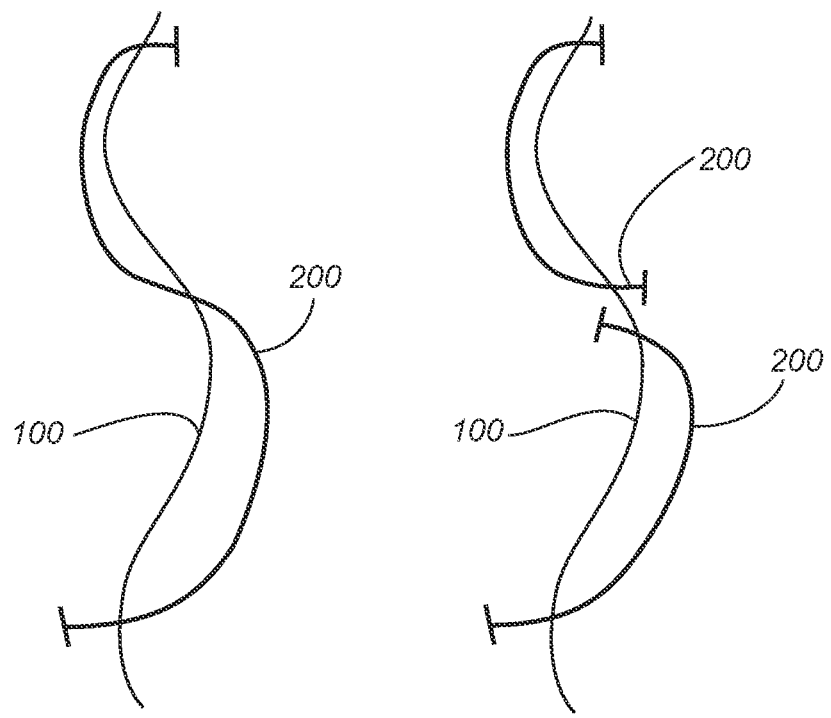
FIG. 5 depicts an exemplary method for shaping a nasal tissue using a tensioning element configured to act on multiple regions of a target nasal tissue.

As shown in FIG. 5, in some embodiments the method may be configured to alter the shape of a nasal tissue in multiple regions. In some embodiments, the method may be configured to utilize a single tensioning element (200) that is configured to act on multiple regions of the target nasal tissue. In some embodiments, the method may be configured to utilize more than one tensioning element to act on multiple regions of the target nasal tissue. In some embodiments, the method may be configured to alter the shape of multiple nasal tissues. In some embodiments, the method may be configured to alter the shape of multiple nasal tissues in multiple regions.

Although the systems, devices, and methods herein have been described with particular application with altering the shape of nasal tissues, it will be appreciated that the devices and systems described herein may be introduced into other natural or surgically-created body passages to alter other tissue structures. In addition, the devices, systems, and methods herein may also be used to alter the shape of tissue structures without requiring introduction into a subject's body, such as ears and the like.

Further, it will be appreciated that elements or components shown with any embodiment herein are exemplary for the specific embodiment and may be used on or in combination with other embodiments disclosed herein.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

The invention claimed is:

1. A method for reshaping a nasal septum of a subject, comprising:
   deploying an elongate shaping element into a nasal septal tissue, the shaping element having a relaxed state and a tensioned state, and comprising a first end having an anchor thereon, a second end, and one or more migration prevention elements along an intermediate region between the first and second ends;
   securing the anchor of the shaping element to tissue adjacent the nasal septal tissue;
   applying a force to the shaping element to alter the shape of the nasal septal tissue; and
   anchoring the shaping element in its tensioned state.

2. The method of claim 1, wherein the nasal septal tissue comprises a nasal septal cartilage.

3. The method of claim 1, wherein the nasal septal tissue comprises a nasal septal bone.

4. The method of claim 1, wherein the applied force alters the shape of a deviated nasal septum.

5. The method of claim 4, wherein the deviated nasal septum comprises a C-shaped deviation, an S-shaped deviation, a sagittal deviation, a coronal deviation, or an anterior caudal deviation of the nasal septum.

6. The method of claim 1, wherein the altered shape is used to treat a deviated nasal septum, a dislocated nasal septum, a nasal septal fracture, a subluxation of septal cartilage, a bony deformation of the nasal septum, a cartilaginous deformation of the nasal septum, or combinations thereof.

7. The method of claim 1, wherein the applied force ranges from about 4 Newtons to about 40 Newtons.

8. The method of claim 7, wherein the applied force ranges from about 12 Newtons to about 25 Newtons.

9. The method of claim 1, wherein applying a force to the shaping element comprises applying tension to the second end of the shaping element.

10. The method of claim 1, further comprising securing the second end of the shaping element to tissue adjacent the nasal septum after applying the force.

11. The method of claim 10, wherein securing the second end of the shaping element maintains the altered shape of the nasal septal tissue.

12. The method of claim 10, wherein securing the second end comprises directing the second end through the nasal septal tissue at a location spaced apart from the first end.

13. The method of claim 10, wherein the first end is secured to the nasal septal tissue on one side of a deviated septum, wherein the second end is secured to the nasal septal tissue on an opposite side of the deviated septum, and wherein the force is applied to alter the shape of the deviated septum.

14. The method of claim 10, wherein the first end is secured to the nasal septal tissue distal to a deviated septum, wherein the second end is secured to the nasal septal tissue proximal to the deviated septum, and wherein the force is applied to alter the shape of the deviated septum.

15. The method of claim 1, wherein the anchor comprises a T-fastener, an X-shaped fastener, an expandable anchor, a button, a shape-retaining structure, a barb, or a combination thereof.

16. The method of claim 1, wherein the anchor is adjustable along the shaping element relative to the first end.

17. The method of claim 1, further comprising directing the shaping element through the nasal septal tissue using a needle on the second end.

18. The method of claim 1, wherein the shaping element comprises PDO (Poly(dioxanone)).

19. A method for reshaping a nasal septum of a subject, comprising:
   inserting a delivery device into a nasal airway of the subject;
   deploying an elongate shaping element from the delivery device into a nasal septal tissue, the shaping element having a relaxed state and a tensioned state, and comprising a first end, a second end, an anchor secured to the first end, and one or more migration prevention elements along an intermediate region between the first and second ends;
   securing the anchor of the shaping element to tissue adjacent the nasal septal tissue;
   applying a force to the shaping element to alter the shape of the nasal septal tissue; and
   anchoring the shaping element in its tensioned state.

* * * * *